(12) United States Patent
Janda et al.

(10) Patent No.: US 6,664,372 B1
(45) Date of Patent: Dec. 16, 2003

(54) AZATIDE PEPTIDOMIMETICS

(75) Inventors: Kim D. Janda, San Diego, CA (US); Hyunsoo Han, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/142,148

(22) PCT Filed: Mar. 20, 1997

(86) PCT No.: PCT/US97/04963
§ 371 (c)(1),
(2), (4) Date: Sep. 1, 1998

(87) PCT Pub. No.: WO97/35199
PCT Pub. Date: Sep. 25, 1997

Related U.S. Application Data
(60) Provisional application No. 60/013,822, filed on Mar. 20, 1996.

(51) Int. Cl.[7] .......................... C07K 7/00; C07K 16/00; A61K 38/00; G01N 33/53; G01N 33/566
(52) U.S. Cl. .......................... 530/332; 435/7.1; 435/7.2; 435/DIG. 48; 436/501; 436/518; 436/528; 530/323; 530/330; 530/334; 530/335; 530/338
(58) Field of Search ................... 435/7.1, 7.2, DIG. 48; 436/501, 518, 528; 530/323, 330, 334, 335, 332, 338

(56) References Cited
FOREIGN PATENT DOCUMENTS
WO    WO 96/03418    2/1996

OTHER PUBLICATIONS

Gordon et al. Applications of Combinatorial Technologies to Drug Discovery. 2. J. Med. Chem., vol. 37, No. 10, pp. 1385–1401, May 1994.*
Colombo, R. New Poly(ethyleneglycol) Supports . . . Tet. Lett., vol. 22, No. 41, pp. 4129–4132, 1981.*
Gallop et al. Applications of Combinatorial Technologies to Drug Discovery. 1. J. Med. Chem., vol. 37, No. 9, pp. 1233–1251, Apr. 1994.*
Bentley, et al., "Polypeptides. Part II. A "Hydrazino–Peptide" Analogue of Norophthalmic Acid Amide", *J. Chem. Soc. (C)*: 60–64 (1966).
Dutta, et al., "Polypeptides. Part XIII. Preparation of α–Aza–amino–acid (Carbazic Acid) Derivatives and Intermediates for the Preparation of α–Aza–peptides", *J. Chem. Soc. Perkin Trans. 1*: 1712–1720 (1975).
Dutta, et al., "Polypeptides. Part 15. Synthesis and Biological Activity of a–Aza–analogues of Luliberin modified in Positions 6 and 10", *J. Chem. Soc. Perkin Trans. 1*: 379–388 (1979).
Gante, "Azapeptides", *Synthesis*: 405–413 (1989).
Quibell, et al., "Synthesis of Azapeptides by the Fmoc/tert–Butyl/Polyamide Technique", *J. Chem. Soc. Perkin Trans. 1*: 2843–2849 (1993).

* cited by examiner

Primary Examiner—Maurie Garcia Baker
(74) Attorney, Agent, or Firm—Donald G. Lewis

(57) ABSTRACT

Peptidomimetic azatides and combinatorial oligoazitide libraries are produced by means of a stepwise synthesis. Combinatorial library construction of this new biomimetic polymer provides a means to fabricate global peptidomimetic libraries.

2 Claims, 21 Drawing Sheets

Peptide

Azapeptide

Azatide

| Compound | R¹ | R² | R³ | R⁴ | Yield (%) |
|---|---|---|---|---|---|
| 5 | H | H | H | H | 92 |
| 6 | Methyl | H | H | Methyl | 91 |
| 7 | H | Methyl | H | Methyl | 90 |
| 8 | H | Methyl | H | Benzyl | 85 |
| 9 | H | Methyl | H | Isobutyl | 84 |
| 10 | H | Isobutyl | H | Isobutyl | 82 |
| 11 | H | Isopropyl | H | Isopropyl | 84 |

1. Starting from 1-R'-Hydrazine Carboxylic Acid, 1,1-Dimethylethyl Ester:
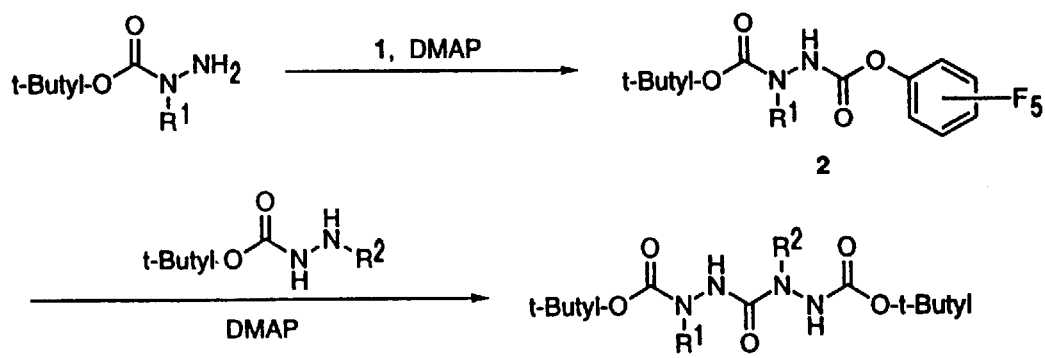
2. Starting from 2-R'-Hydrazine Carboxylic Acid, 1,1-Dimethylethyl Ester:
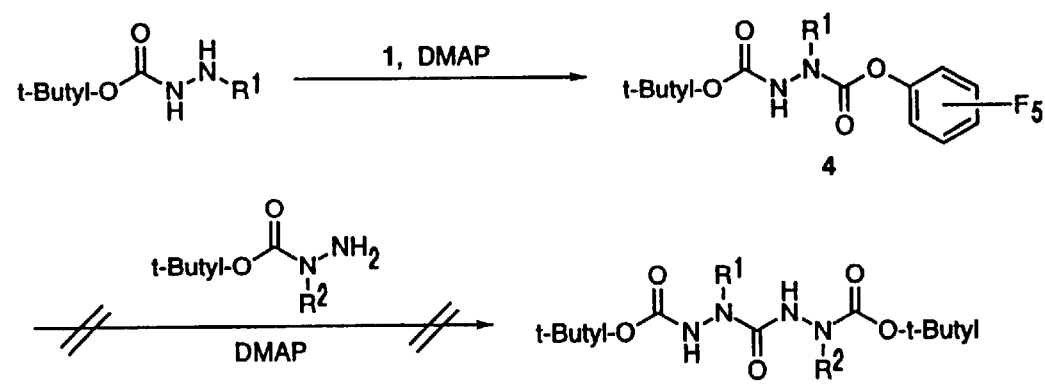
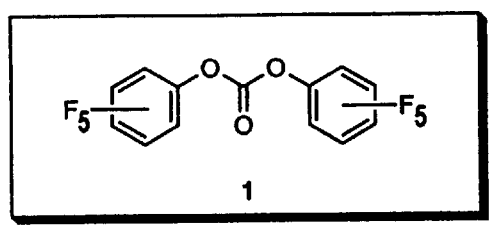
FIG. 3

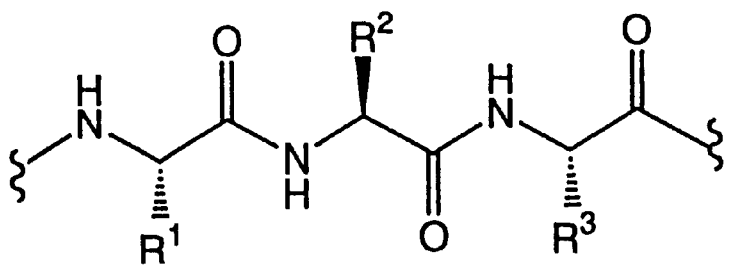
Peptide
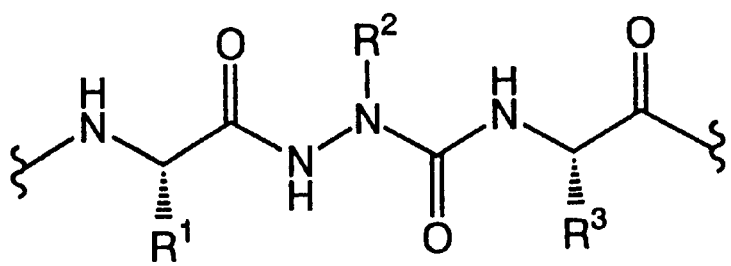
Azapeptide
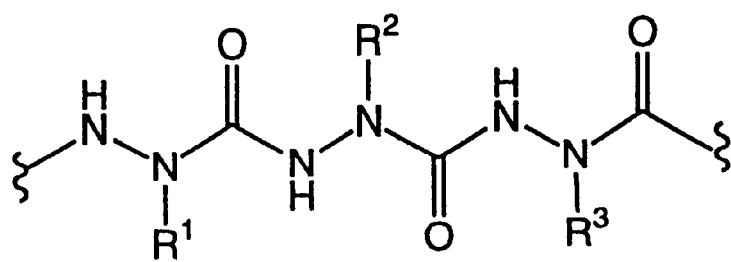
Azatide
FIG. 5

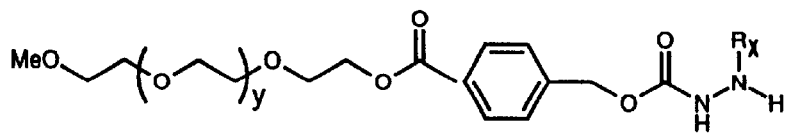

Nascent deprotected chain of length 1; compound 18

"n" addition molecule added seperately to "n" reaction vessel containing nascent chain (18)

, DMAP

ADDITION MOLECULE x = 1 to n (n = 20 for natural a.a.)

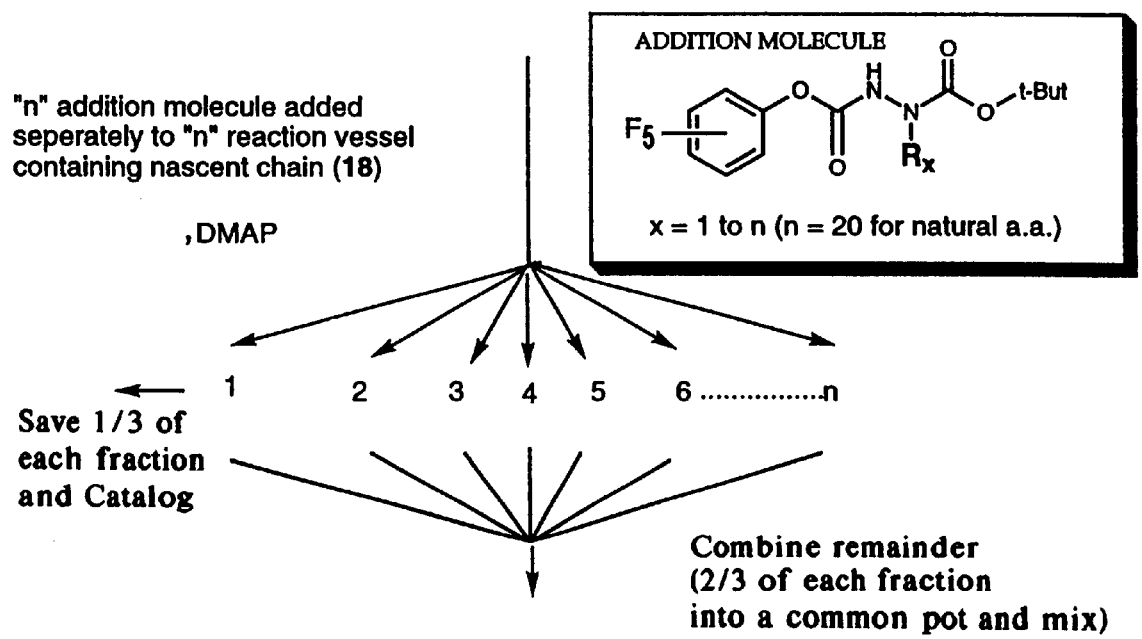

Save 1/3 of each fraction and Catalog

Combine remainder (2/3 of each fraction into a common pot and mix)

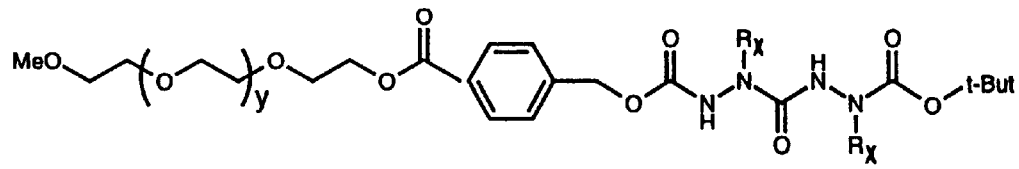

Nascent protected chain of length 2; compound 19

Removal of BOC protecting group | TFA/ CH$_2$Cl$_2$

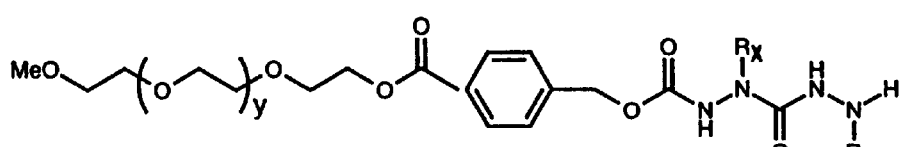

Nascent protected chain of length 2; compound 20

FIG. 9

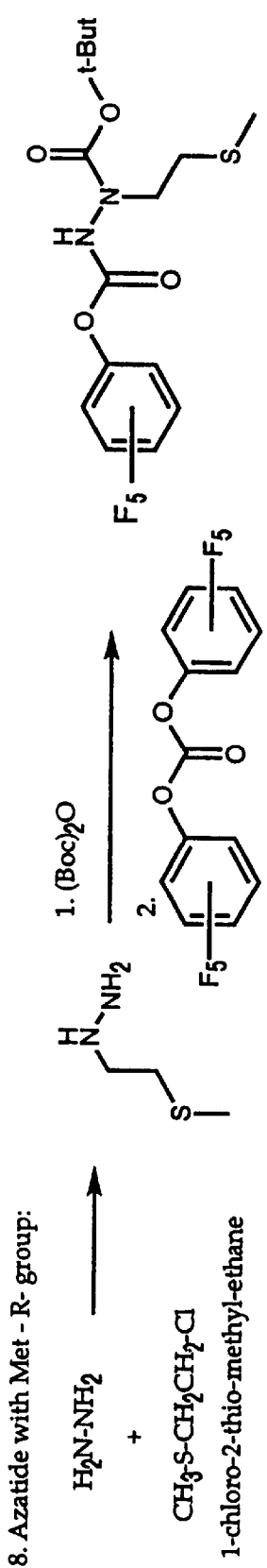
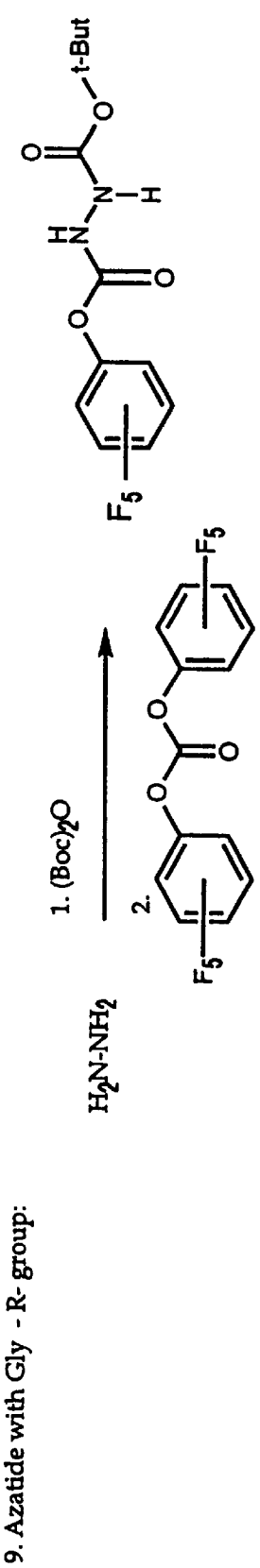
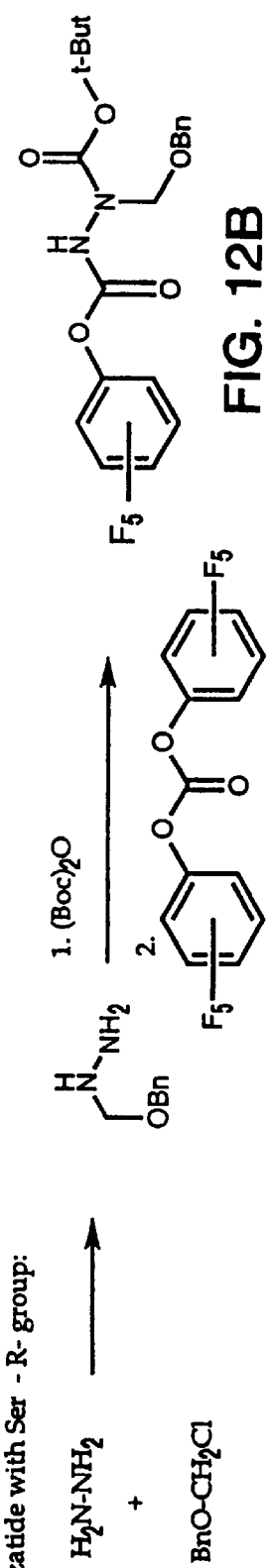
8. Azatide with Met - R- group:
H₂N-NH₂
+
CH₃-S-CH₂CH₂Cl
1-chloro-2-thio-methyl-ethane
9. Azatide with Gly - R- group:
H₂N-NH₂
10. Azatide with Ser - R- group:
H₂N-NH₂
+
BnO-CH₂Cl
FIG. 12B

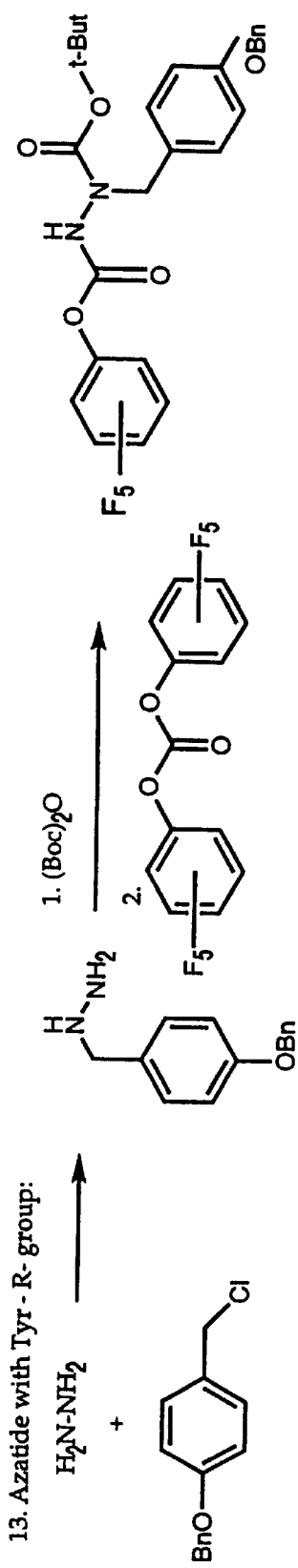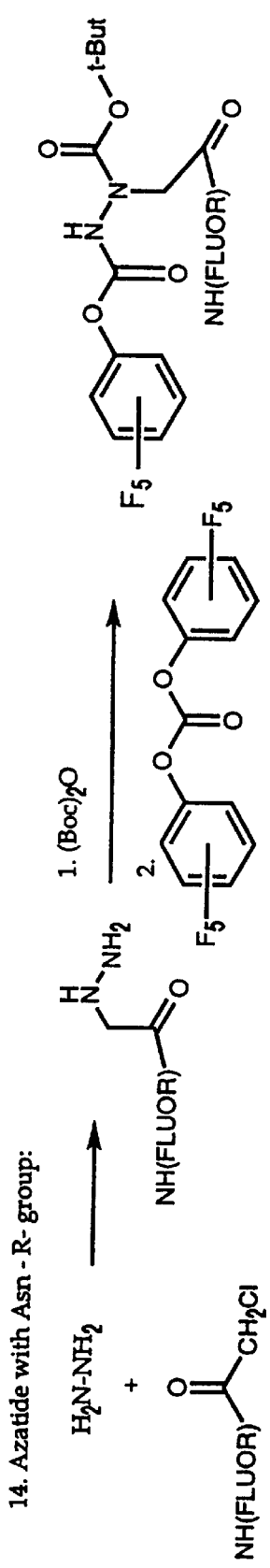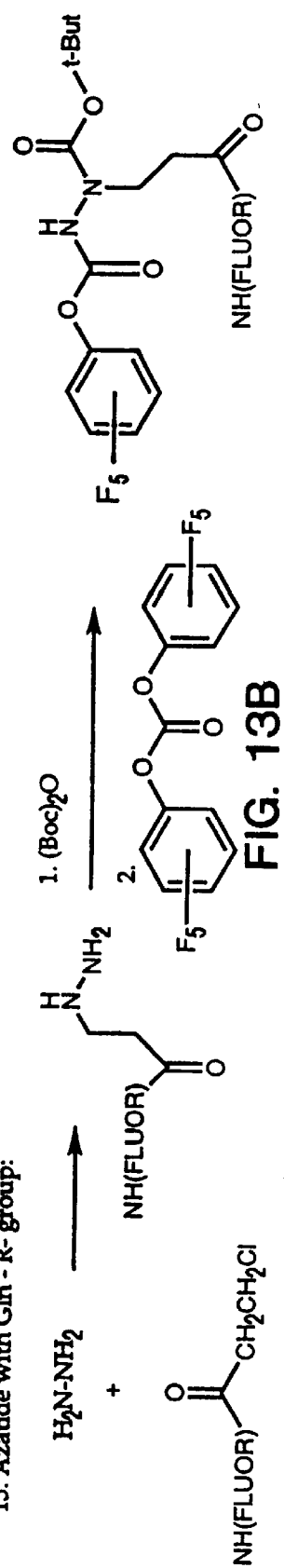
FIG. 13B

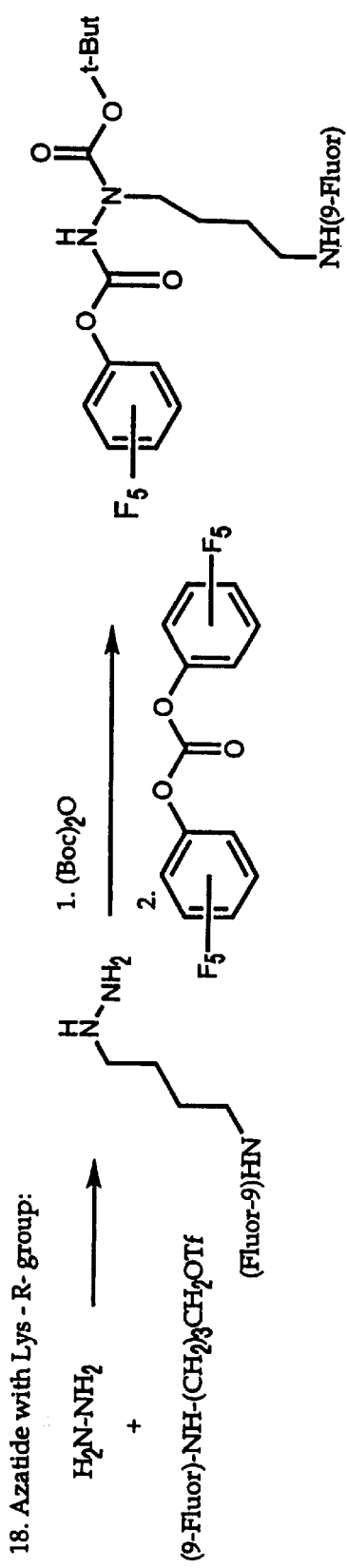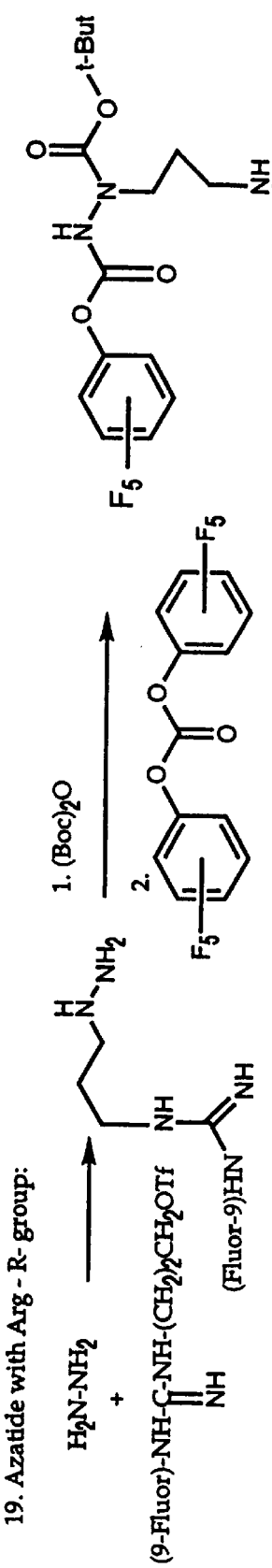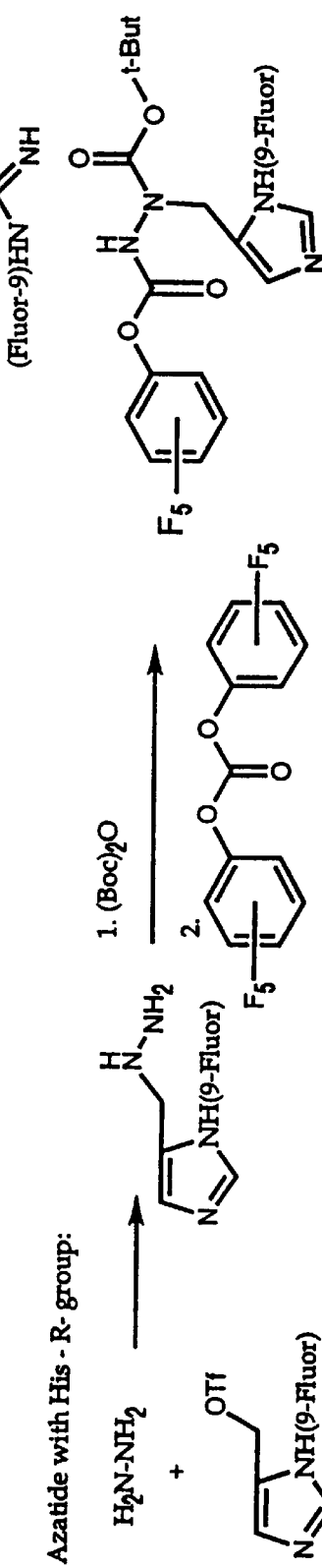
FIG. 14B

Azatide with Asp - R- group:
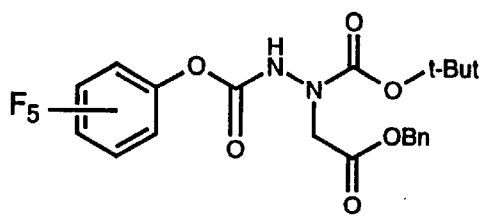
Azatide with Phe - R- group:
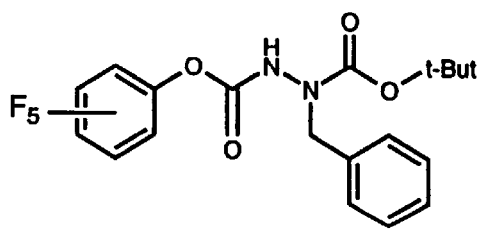
Azatide with Glu - R- group:
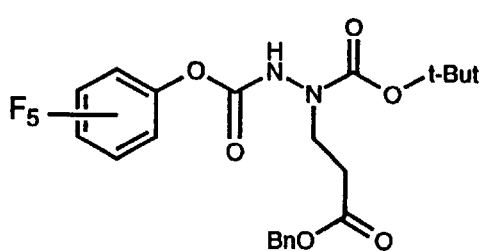
Azatide with Trp - R- group:
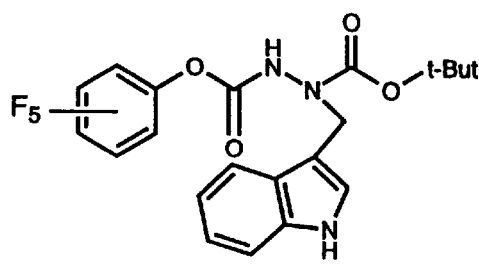
Azatide with Lys - R- group:
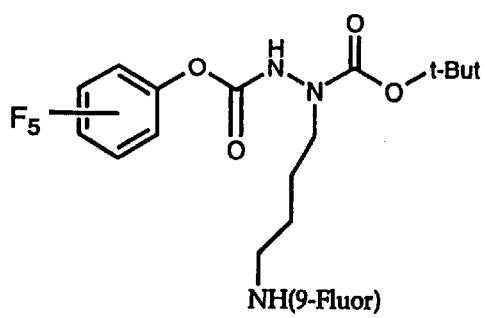
Azatide with Met - R- group:
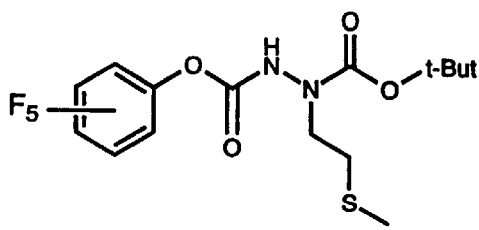
Azatide with Arg - R- group:
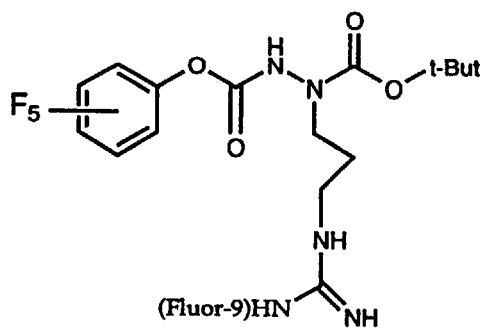
Azatide with Gly - R- group:
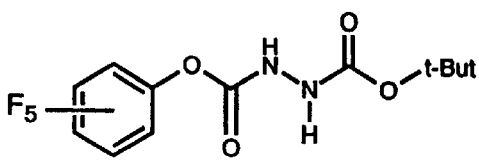
Azatide with Ser - R- group:
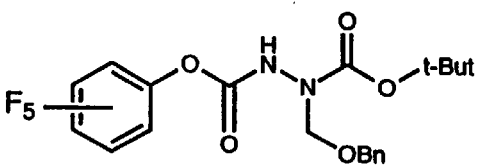
Azatide with His - R- group:
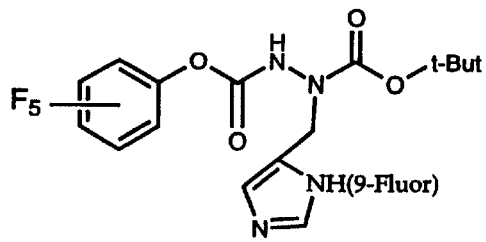
FIG. 15

Azatide with Thr - R- group:
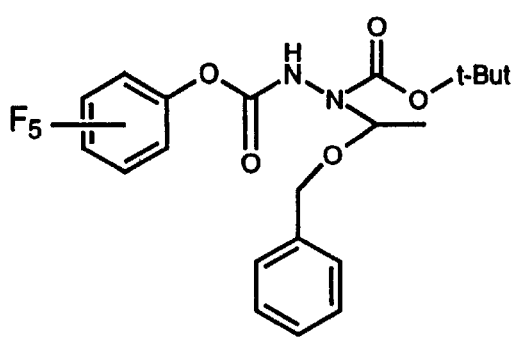
Azatide with Ala - R- group:
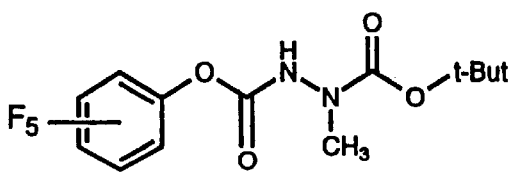
Azatide with Cys - R- group:
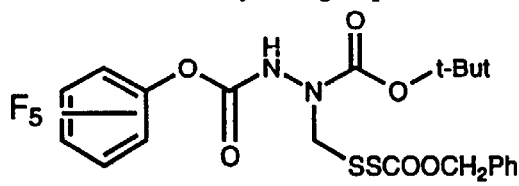
Azatide with Val - R- group:
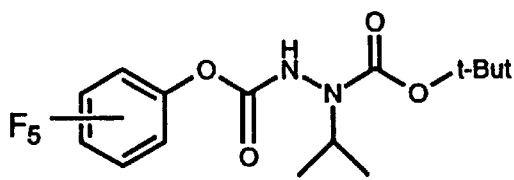
Azatide with Tyr - R- group:
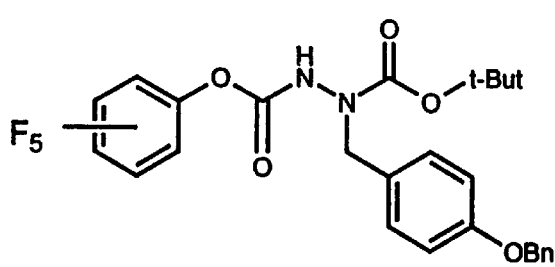
Azatide with Leu - R- group:
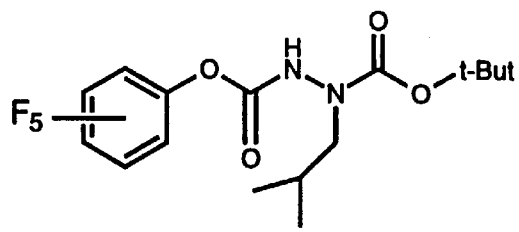
Azatide with Asn - R- group:
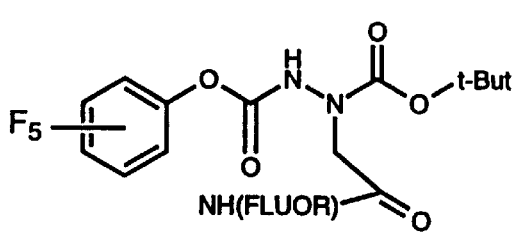
Azatide with Ile - R- group:
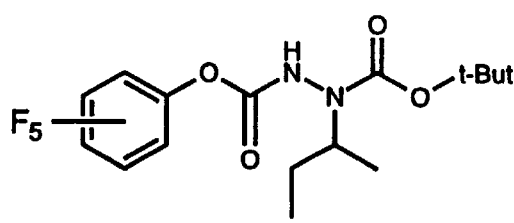
Azatide with Gln - R- group:
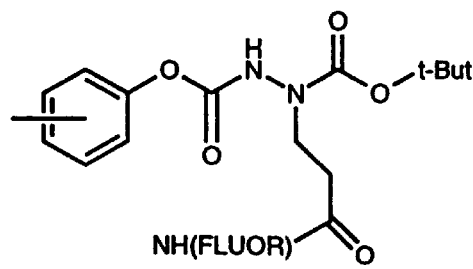
Azatide with Pro - R- group:
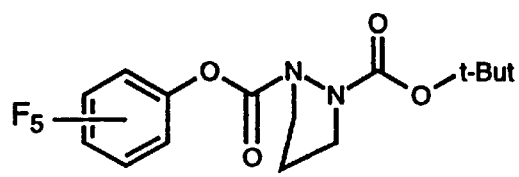
FIG. 16

SEQUENCE LISTING

```
<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: synthesized

<400> SEQUENCE: 1

Tyr Gly Gly Phe Leu
1               5

<210> SEQ ID NO 2
<211> LENGTH: 4
<212> TYPE: PRT
<213> ORGANISM: Artificial Sequence
<220> FEATURE:
<223> OTHER INFORMATION: synthesized

<400> SEQUENCE: 2

Tyr Gly Gly Phe
1

<210> SEQ ID NO 3
<211> LENGTH: 5
<212> TYPE: PRT
<213> ORGANISM: Artificial Sequence
<220> FEATURE:
<223> OTHER INFORMATION: synthesized
<220> FEATURE:
<223> OTHER INFORMATION: C-terminal modification:
      NH-(CH2)2-NH-CO-(CH2)2-SS-BSA

<400> SEQUENCE: 3

Tyr Gly Gly Phe Leu
1               5
```

AZATIDE PEPTIDOMIMETICS

CROSS-REFERENCE TO RELATED APPLICATIONS

The present application claims priority from and is a national stage application under 35 U.S.C. §371 of copending International Application No. PCT/US97/04963, filed Mar. 20, 1997 and published in English on Sep. 25, 1997, which claims priority, under 35 U.S.C. §119(e), from provisional application Ser. No. 60/013,822, filed Mar. 20, 1996, now abandoned.

TECHNICAL FIELD

The present invention relates to compounds that mimic peptides. More particularly, the present invention relates to the synthesis of peptides in which α-carbons of the peptide backbone have been replaced by trivalent nitrogen atoms using either solution phase or liquid phase synthetic methodologies.

BACKGROUND

Peptidomimetics have become immensely important for both organic and medicinal chemists (Spatola et al. *Chemistry and Biochemistry of Amino Acids, Peptides, and Proteins*; Weinstein, B., Ed.; Marcel Dekker: New York, 1983; pp. 267–357; Sherman et al. *J. Am. Chem. Soc.* 1990, 112, 433; Hirschmann et al. *Angew. Chem. Int. Ed. Engl.* 1990, 29, 1278; Gante et al. *Angew. Chem. Int. Ed. Engl.* 1994, 33, 1699). Synthetic interest in these surrogate peptide structures has been driven by the pharmaceutical industry's needs for molecules with improved pharmacokinetic properties (Hodgson et al. *Bio/Technology* 1993, 11, 683). Biophysical studies on these pseudopeptides has allowed elucidation of the functional role of the peptide backbone (Marshall et al. *Chemical Recognition in Biological Systems*; Creighton et al. The Chemical Society: London, 1982; p 278; Farmer et al. *Drug Design*; Ariens, E. J., Ed.; Academic Press, New York, 1980, p. 121) and with an ever-increasing level of synthetic sophistication the degree of peptide mimicry within a peptidomimetric can be tailored to chemist's needs. Indeed, the alteration of peptides to peptidomimetics has included peptide side chain manipulations, amino acid extensions (Freidinger et al. *Science* 1980, 210, 656; Paruszewski et al. *Rocz. Chem.* 1973, 47, 735; Stachowiak et al. *J. Med. Chem.* 1979, 22, 1128), deletions (Rivier et al. *Chemia* 1972, 26, 303; Sarantakis et al. *Clin. Endocrinol.* 1976, 5, 2755), substitutions, and most recently backbone modifications (Hagihara et al. *J. Am. Chem. Soc.* 1992, 114, 6568; Simon et al. *Proc. Natl. Acad. Sci. USA* 1992, 89, 9367; Smith et al. *J. Am. Chem. Soc.* 1992, 10 114, 10672; Cho et al. *Science* 1993, 261, 1303; Liskamp et al. *Angew. Chem. Int. Ed. Engl.* 1994, 33, 633; Burgess et al. *Angew. Chem. Int. Ed. Engl.* 1995, 34, 907). It is this latter development that has been exploited for the synthesis of biomimetic polymeric structures. Such progress has been fueled by the suggestion that peptidomimetics may provide novel scaffolds for the generation of macromolecules with new properties of both biological and chemical interest.

The most common manipulation involving the α-carbon atom of peptides is the inversion of stereochemistry to yield D-amino acids (Spatola et al. *Chemistry and Biochemistry of Amino Acids, Peptides, and Proteins*; Weinstein, B., Ed.; Marcel Dekker: New York, 1983; pp. 267–357). The importance of this substitution in affording compounds with improved biological potencies, altered conformational properties (Mosberg et al. *Proc. Natl. Acad. Sci. USA* 1983, 80, 5871), and increased resistance to enzymatic degradation has been widely recognized and exploited (Dooley et al. *Science* 1994, 266, 2019). Replacement of the α-hydrogen of the common amino acids by a methyl group, or by any other substituents ($NH_2CRR'CO_2H$) are both further examples of α-alkyl modification. Azapeptides, however, are peptides in which one (or more) of the α-carbon(s) has been replaced by a trivalent nitrogen atom (FIG. 5) (Gante et al. *Synthesis* 1989, 405). This transformation results in a loss of asymmetry associated with the α-carbon and yields a structure that can be considered intermediate in configuration between D- and L- amino acids (Aubry et al. *Biopolymers* 1989, 28, 109). Interest in this α-carbon replacement unit stems from its ability to provide resistance to enzymatic cleavage and its capacity to act as a selective inhibitor of cysteine (Magrath et al. *J. Med. Chem.* 1992, 35, 4279) and serine proteases (Elmore et al. *Biochem. J.* 1968, 107, 103; Barker et al. *Biochem. J.* 1974, 139, 555; Gray et al. *Tetrahedron* 1977, 33, 837; Gupton et al. *J. Biol. Chem.* 1984, 259, 4279; Powers et al. *J. Biol. Chem.* 1984, 259, 4288). While the synthesis of azapeptides has been reported (Bentley et al. *J. Chem. Soc.* (C) 1966, 60; Dutta et al. *J. Chem. Soc. Perkin Trans 1* 1975, 1712; Furr et al. *J. Chem. Soc. Perkin Trans 1* 1979, 379; Quibell et al. *J. Chem. Soc. Perkin Trans 1* 1993, 2843), the synthesis of a "pure azapeptide", or what we will term an "azatide" has yet to be accomplished. The earliest attempts to make pure azatides can be dated to Gante and co-workers. (Gante et al. *Chem. Ber.* 1965, 98, 3340; Gante et al. *Proc. Am. Pept. Symp.* 13th. 1993, 1994, 299) However, the methodology that was reported does not allow azatide stepwise chain lengthening in a repetitive manner of anything but hydrazine units.

The utility of azatide compounds has been demonstrated in the treatment of various disorders including cancers, viral infections and cataracts. For example, Moretti et al, *J. Clin. Endocrino. Metab.*, 81(11), 3930–3937, 1996, show that azatide compounds are used as LH-releasing hormone agonists to interfere with stimulatory actions of epidermal growth factor in human prostatic cancer cell lines. Jeyarajah et al, *Gynecol. Oncol.*, 63(1), 47–52, 1996, use an azatide gonadotropin-releasing hormone analog for treatment of recurrent endometrial cancers. Brower et al, *J. Surg. Res.*, 52(1), 6–14, 1992, show differential effects of azatide containing LHRH and somatostatin analogs on human breast cancers. Hellberg et al., PCT Int. Appl. WO 9640107 A1 961219, demonstrate the use of (N,N'-bis(mercaptoacetyl) hydrazine derivatives as anticataract agents. Nakashima et al., EP 672678 A1 950920, show the preparation and use of azapeptide compounds as neurokinin A antagonists. Azatide type compounds have been used as retroviral protease inhibitors, Kempf et al., PCT Int. Appl. WO 9414436 A1 940707, lipoxygenase inhibitors (Atkinson et al Eur. Pat. Appl. EP 146243 A1 850626) and immunosuppressant rapamycin carbamate analogs, Kao et al. U.S. application Ser. No. 5,411,967A 950502.

What is needed is either a solution phase or liquid phase synthetic methodology for synthesizing azatides using monomeric "α-aza-amino acids" which can be coupled in a linear and stepwise chain-lengthening fashion. What are needed are azatides as mimetics for peptides which are are easy to synthesize, more stable and more active than the parent peptides. Moreover, azatide mimetics are needed for stability as compared to various natural peptide products and compounds which possess better bioavailability and exhibit greater activity as compared to known peptides.

SUMMARY OF THE INVENTION

The invention is directed to the azatides and a method for the synthesis of azatide mimetics. In particular, an efficient method has been developed for the solution and liquid phase syntheses of biopolymer mimetics consisting of "α-aza-amino acids" linked in a repetitive manner to form an azatide oligomer. A general synthetic procedure is claimed which provides the use and synthesis of a wide variety of Boc-protected aza-amino acid monomers with optimization of solution phase procedures for the coupling of aza-amino acids in a repetitive manner. In addition, the design and synthesis of a linker is employed that supports azatide synthesis using a liquid phase synthetic format. Oligoazatides can now be rapidly assembled on a homogeneous polymeric support. Using the methodology provides a potential source of new peptidomimetic libraries.

One aspect of the invention is directed to a process for synthesizing an oligoazatide. The process employs a support material with a linker unit attached thereto. The preferred support material is a soluble homopolymer support, e.g., polyethylene glycol monomethyl ether (MeO-PEG). Polyethylene glycol monomethyl ether is soluble in aqueous media but precipitates in ether. Precipitation of the support material with ether can be employed for purifying coupled molecules. Alternative soluble supports having this property are caonventional and may be readily substituted for the polyethylene glycol monomethyl ether. Solid phase supports may also be employed but are less preferred because of their poorer yields and/or difficulty in handling.

A linker unit is attached attached to the soluble support. A preferred linker unit is p-hydroxymethylbenzoate. The process also employs a Boc-protected aza-amino acid. Preferred Boc-protected aza-amino acids are represented by the following structure:

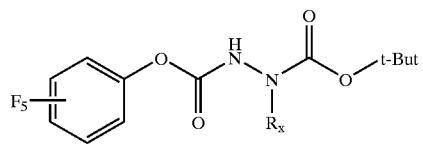

wherein $R_x$ is selected from the group consisting of hydrogen, methyl, isobutyl, isopropyl, $C_1$–$C_6$ alkyl, substituted benzyl and the side chain radical of the following amino acids: Ala, Arg, Asn, Asp, Asx, Cys, Gln, Glu, Glx, Gly, His, Ile, Leu, Lys, Met, Phe, Pro, Ser, Thr, Trp, Tyr and Val. The Boc-protected aza-amino acid is reacted with a carbonyl activation element for producing an activated carbamate of the Boc-protected aza-amino acid. A preferred carbonyl activation element is bis-pentafluorophenyl carbonate. The soluble homopolymer support is then coupled with the activated carbamate for producing a nascent protected chain. The nascent protected chain may then be deprotected using a mild acid for producing a nascent deprotected chain. A preferred mild acid for the deprotection step is trifluoroacetic acid. The nascent deprotected chain is then washed by precipitation of the soluble homopolymer. The nascent deprotected chain may then be extended by repeating the above "n" times wherein $1 \leq n \leq 100$ and wherein the soluble homopolymer support of said Step A is replaced with the nascent deprotected chain for producing an extended deprotected chain. Then, the extended deprotected chain is decoupled from the soluble support by hydrogenation for producing the oligoazatide.

Another aspect of the invention is directed to a process for producing a combinatorial oligoazatide library. The process employs "n" reaction vessels wherein nascent chains are extended by the addition respectively of the activated carbamates of "n" Boc-protected aza-amino acids. After each extension step, aliquots of the products are saved and cataloged and the remainder is pooled into a common pot to form a mixture. The mixture of nascent chains is then aliquoted into "n" reaction vessels for further extension. After "m" extensions, the product is decoupled and separated from the soluble support to form the combnatorial oligoazatide library.

Another aspect of the invention is directed to a combinatorial oligoazatide library. The library comprising a plurality of compounds represented by the following formula:

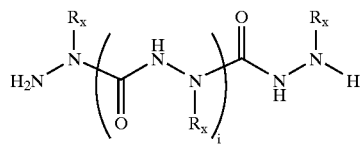

wherein $0 \leq i \leq 99$ and $R_x$ is selected from the group consisting of hydrogen, methyl, isobutyl, isopropyl, $C_1$–$C_6$ alkyl, benzyl, substituted benzyl and the side chain radical of the following amino acids: Ala, Arg, Asn, Asp, Asx, Cys, Gln, Glu, Glx, Gly, His, Ile, Leu, Lys, Met, Phe, Pro, Ser, Thr, Trp, Tyr and Val.

Another aspect of the invention is directed to an azatide compounds represented by the following formulas:

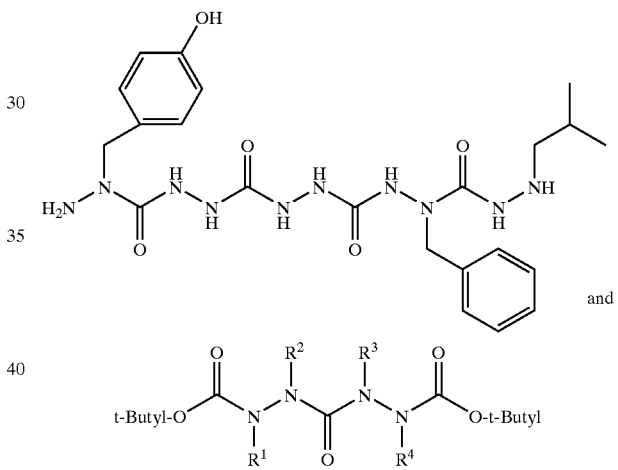

and wherein $R_1$, $R_2$, $R_3$ and $R_4$ is selected from the group consisting of hydrogen, methyl, isopropyl, isobutyl and benzyl.

Another aspect of the invention is directed to intermediate oligoazatide compounds represented by the following formula:

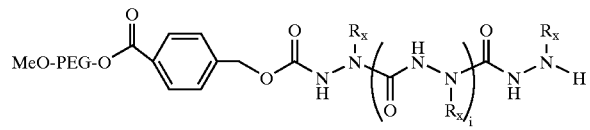

wherein $0 \leq i \leq 99$ and $R_x$ is selected from the group consisting of hydrogen, methyl, isobutyl, isopropyl, $C_1$–$C_6$ alkyl, benzyl, substituted benzyl and the side chain radical of the following amino acids: Ala, Arg, Asn, Asp, Asx, Cys, Gln, Glu, Glx, Gly, His, Ile, Leu, Lys, Met, Phe, Pro, Ser, Thr, Trp, Tyr and Val.

Figure 2:
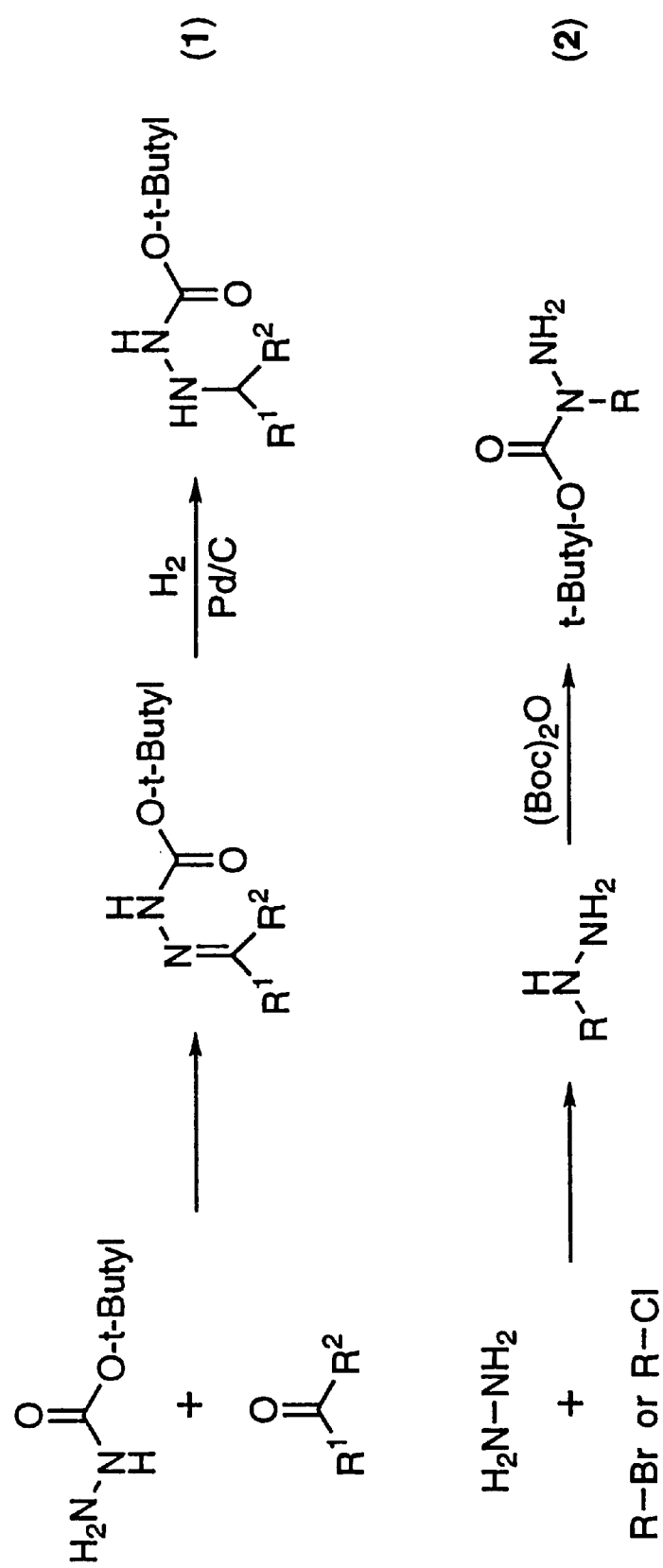

FIG. 2 illustrates the preparation of Boc-protected alkylhydrazine monomers wherein R, $R^1$ and $R^2$ are selected from the group consisting of hydrogen, methyl, isobutyl, isopropyl, benzyl, and the side chain radical of the following amino acids: Ala, Arg, Asn, Asp, Asx, Cys, Gln, Glu, Glx, Gly, His, Ile, Leu, Lys, Met, Phe, Pro, Ser, Thr, Trp, Tyr and Val.

FIG. 3 illustrates various routes for solution phase diazatide synthesis wherein $R^1$ and $R^2$ are selected from the group consisting of hydrogen, methyl, isobutyl, isopropyl, benzyl, and the side chain radical of the following amino acids: Ala, Arg, Asn, Asp, Asx, Cys, Gln, Glu, Glx, Gly, His, Ile, Leu, Lys, Met, Phe, Pro, Ser, Thr, Trp, Tyr and Val.

Figure 4A:
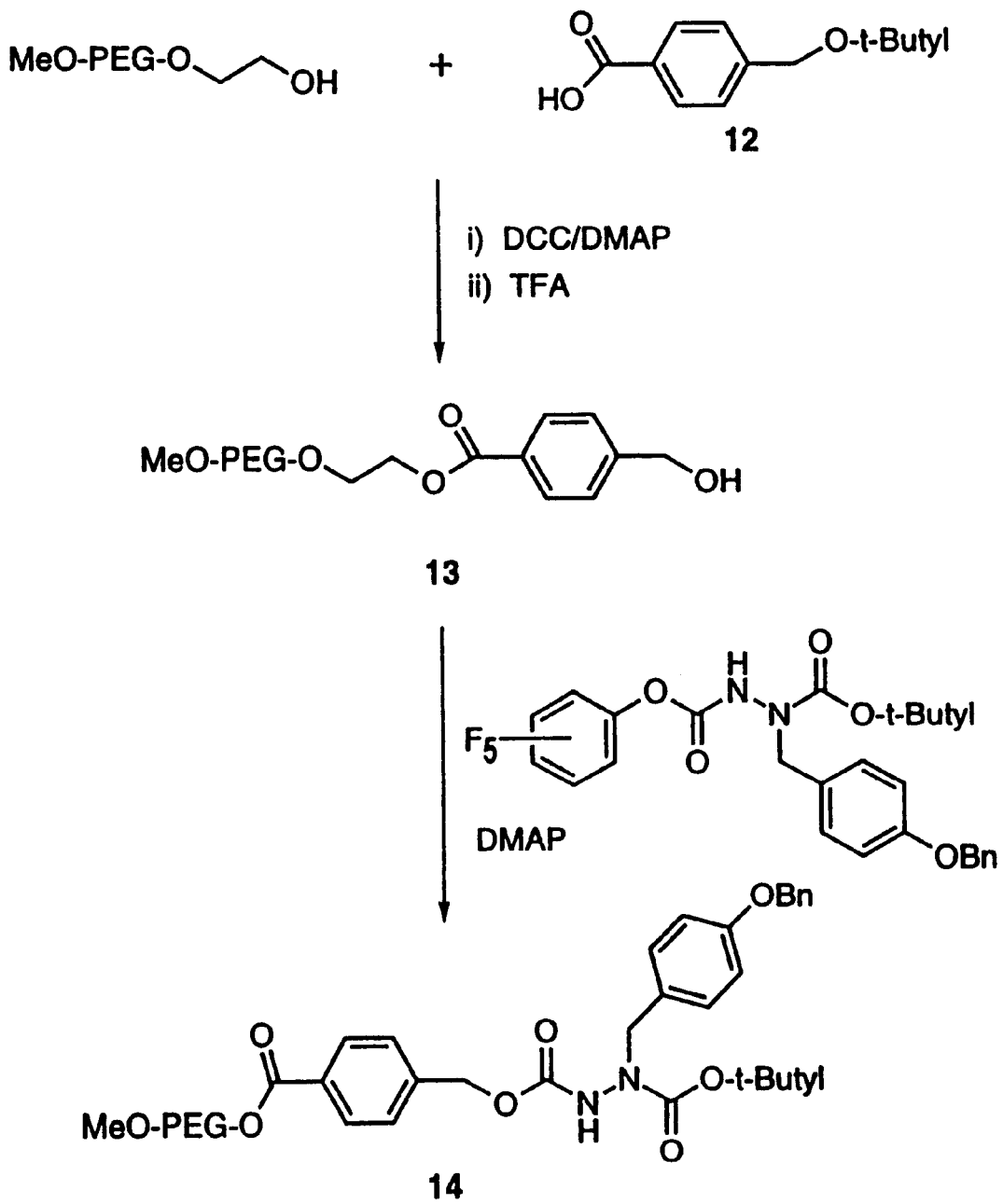
Figure 4B:
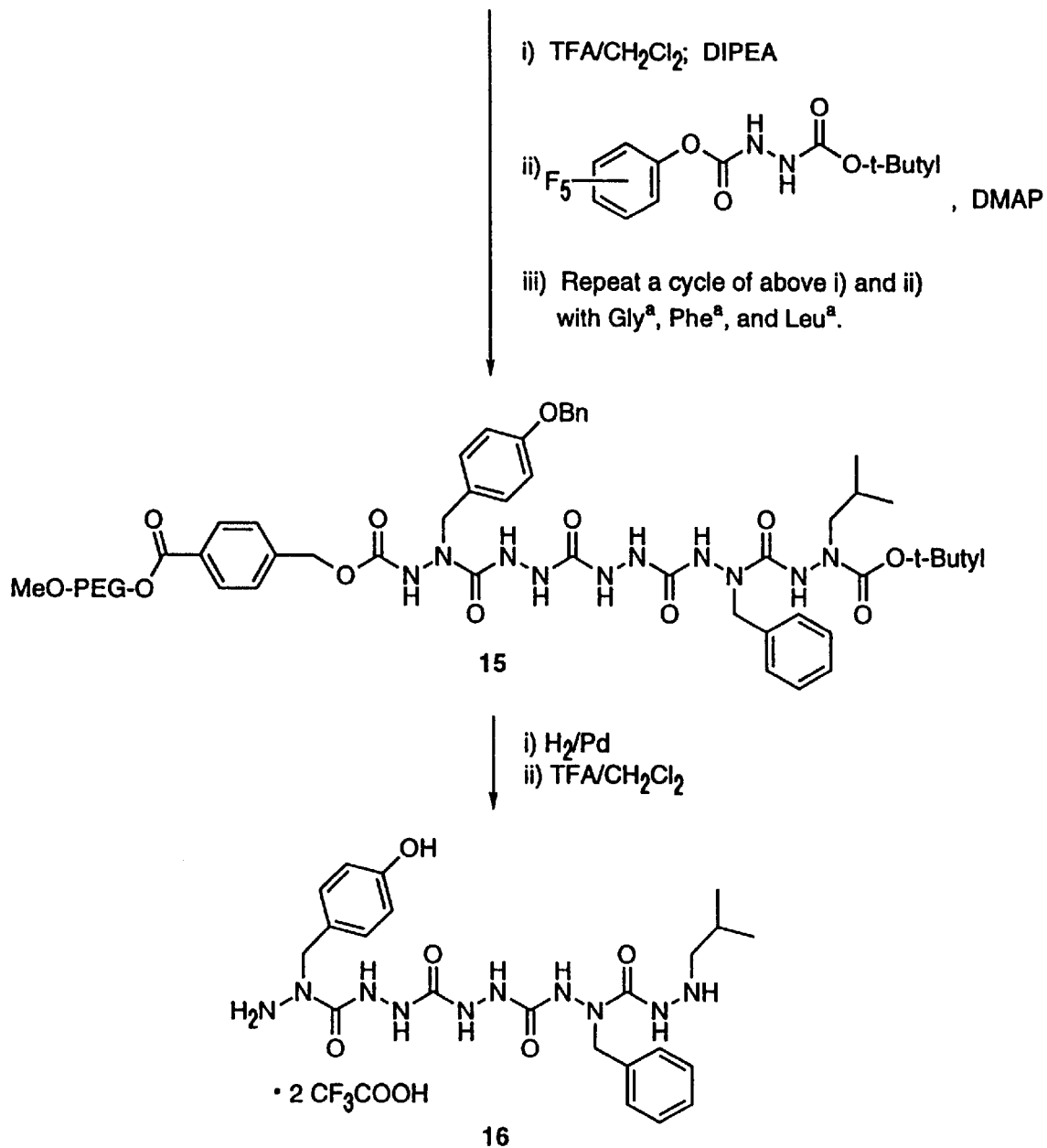

FIGS. 4A and 4B illustrate the synthesis of a MeO-PEG-supported Leu-enkephalin azatide mimetic.

FIG. 5 illustrates the comparison of a peptide, azapeptide, and azatide wherein $R^1$, $R^2$ and $R^3$ are selected from the group consisting of hydrogen, methyl, isobutyl, isopropyl, benzyl, and the side chain radical of the following amino acids: Ala, Arg, Asn, Asp, Asx, Cys, Gln, Glu, Glx, Gly, His, Ile, Leu, Lys, Met, Phe, Pro, Ser, Thr, Trp, Tyr and Val.

Figure 6:
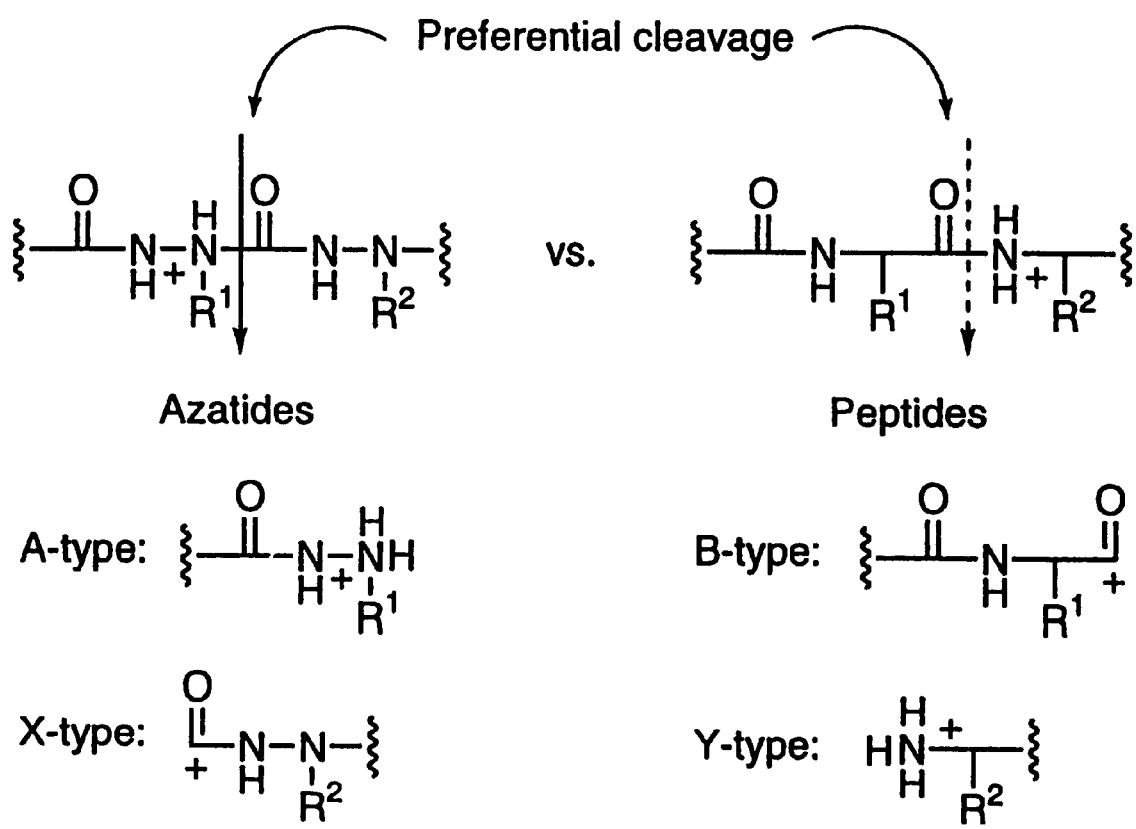

FIG. 6 illustrates the fragmentation patterns of (M+1)+ ion of peptides and azatides wherein $R^1$ and $R^2$ are selected from the group consisting of hydrogen, methyl, isobutyl, isopropyl, benzyl, and the side chain radical of the following amino acids: Ala, Arg, Asn, Asp, Asx, Cys, Gln, Glu, Glx, Gly, His, Ile, Leu, Lys, Met, Phe, Pro, Ser, Thr, Trp, Tyr and Val.

Figure 7A:
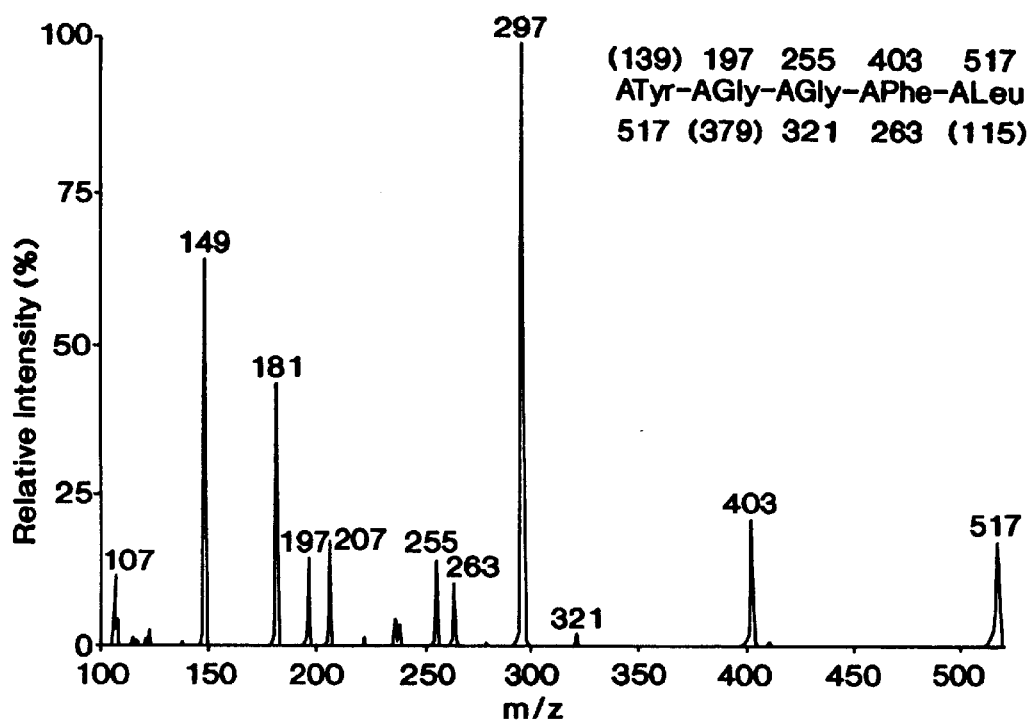
Figure 7B:
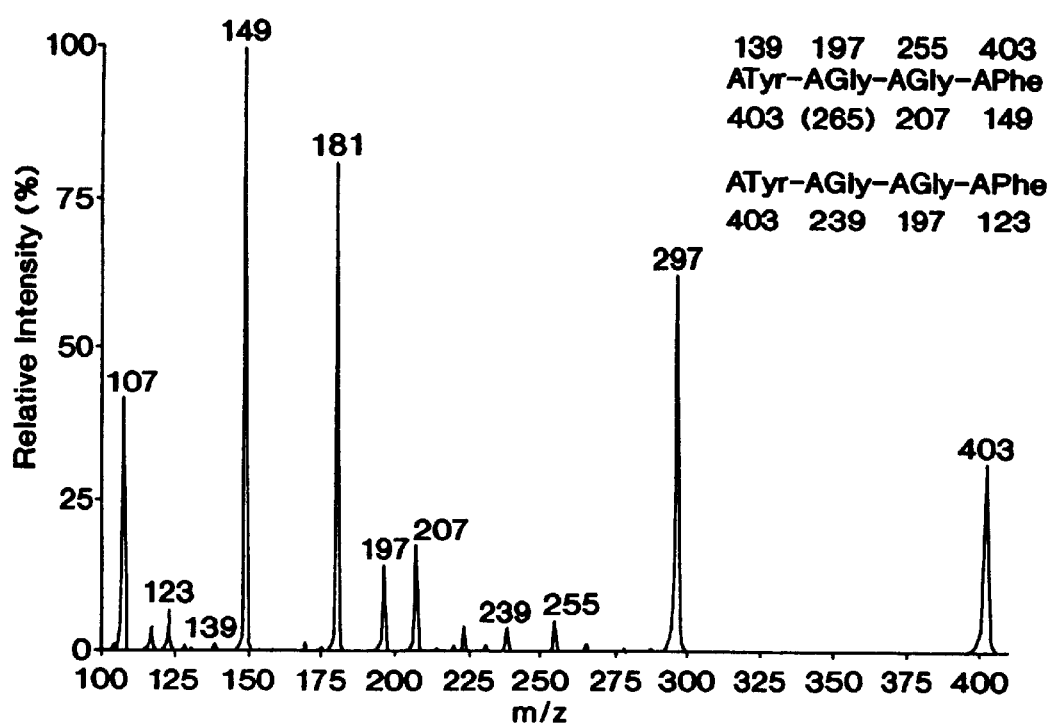

FIGS. 7A and 7B illustrate CAD spectra of m/z 517 $(M+1)^+$ and 403 peaks for compound 16.

Figure 8:
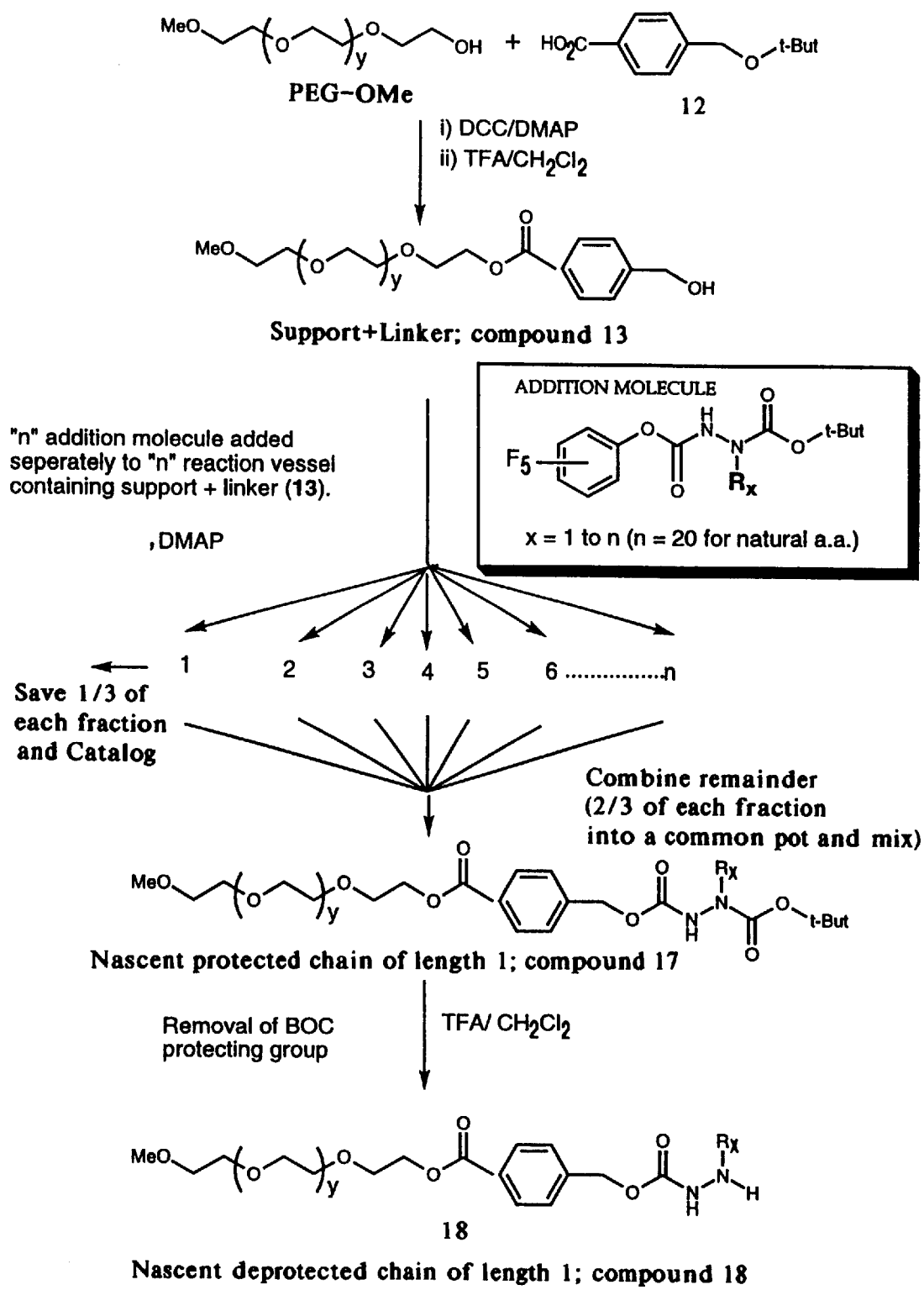

FIG. 8 illustrates a combinatorial strategy for the synthesis of a library of azetide molecules, starting from a support-linker molecule and coupling an 'addition molecule' to such support-linker molecule in a seperate reaction vessel, saving, cataloging, and subsequently recombining each product to form a library of compounds with a nascent protected chain of length 1 wherein $R_x$ is selected from the group consisting of hydrogen, methyl, isobutyl, isopropyl, benzyl, and the side chain radical of the following amino acids: Ala, Arg, Asn, Asp, Asx, Cys, Gln, Glu, Glx, Gly, His, Ile, Leu, Lys, Met, Phe, Pro, Ser, Thr, Trp, Tyr and Val; other functionalities are possible.

FIG. 9 illustrates a combinatorial strategy for the synthesis of a library of azetide molecules, starting from a nascent deprotected chain of length 1 (compound 18) and coupling an 'addition molecule' to such support-linker molecule in a seperate reaction vessel, saving, cataloging, and subsequently recombining each product to form a library of compounds with a nascent protected chain of length 2 wherein $R_x$ is selected from the group consisting of hydrogen, methyl, isobutyl, isopropyl, benzyl, and the side chain radical of the following amino acids: Ala, Arg, Asn, Asp, Asx, Cys, Gln, Glu, Glx, Gly, His, Ile, Leu, Lys, Met, Phe, Pro, Ser, Thr, Trp, Tyr and Val; other functionalities are possible.

Figure 10:
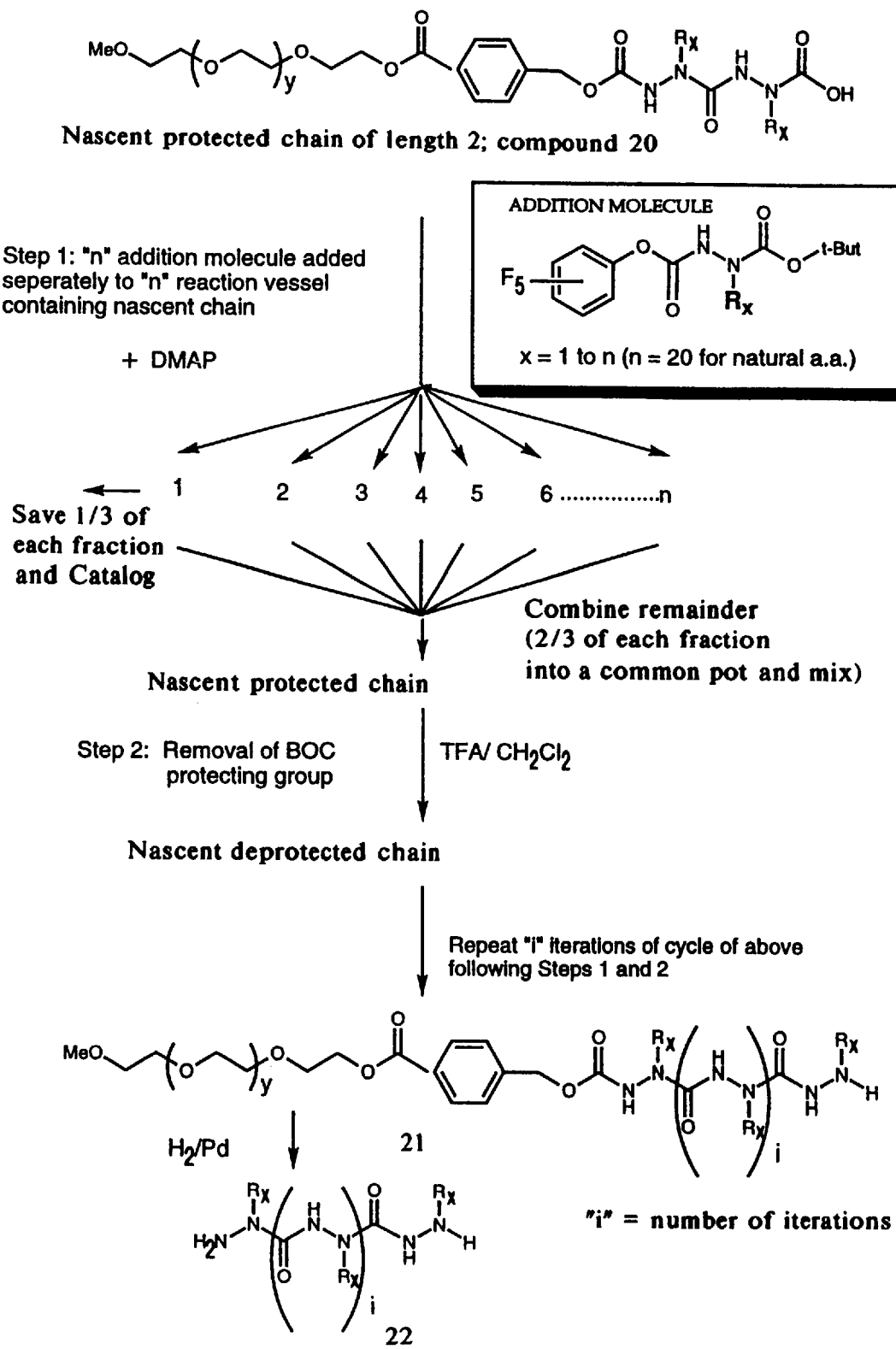

FIG. 10 illustrates a combinatorial strategy for the synthesis of a library of azetide molecules, starting from a nascent deprotected chain of length 2 (compound 20) and coupling an 'addition molecule' to such support-linker molecule in a seperate reaction vessel, saving, cataloging, and subsequently recombining each product and repeating "i" iterations ("i" is an arbitrary number depending on the size of the azetide desired eg. from 0 to 100 cycles) of the cycle of steps 1 and 2 to form a library of azetide products wherein $R_x$ is selected from the group consisting of hydrogen, methyl, isobutyl, isopropyl, benzyl, and the side chain radical of the following amino acids: Ala, Arg, Asn, Asp, Asx, Cys, Gln, Glu, Glx, Gly, His, Ile, Leu, Lys, Met, Phe, Pro, Ser, Thr, Trp, Tyr and Val; other functionalities are possible.

Figure 11A:
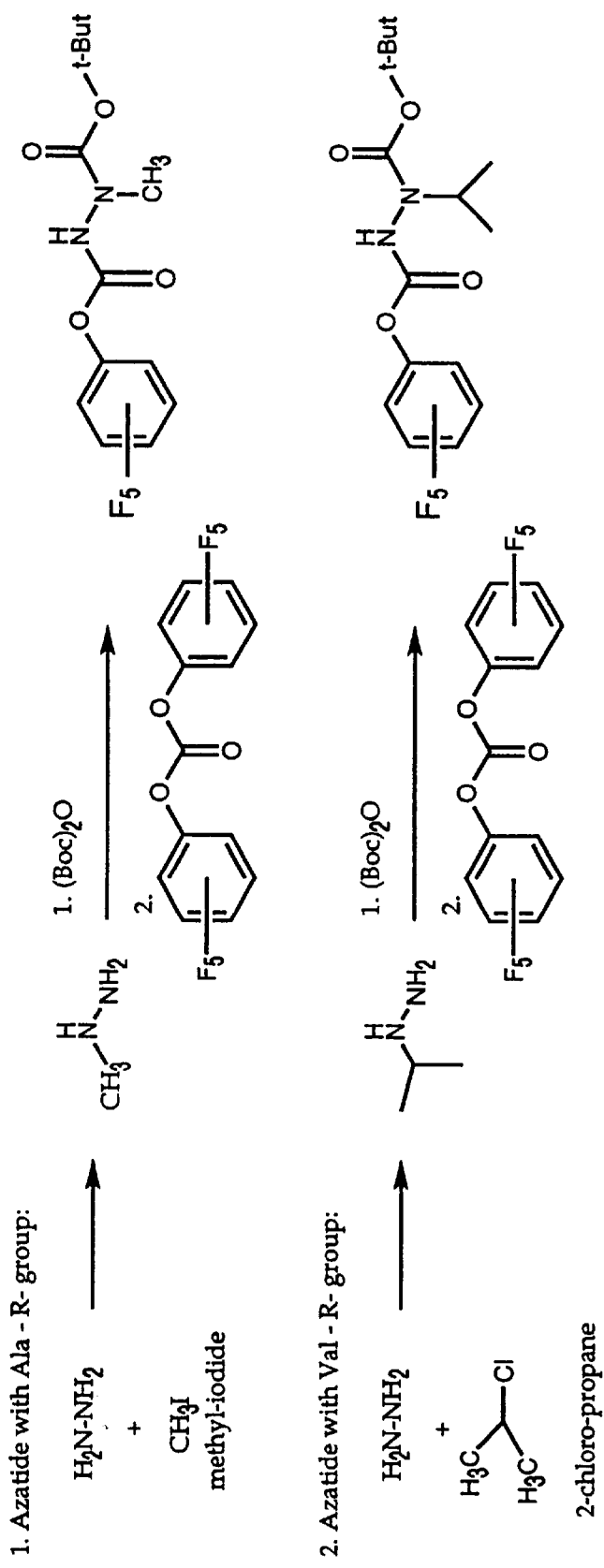
Figure 11B:
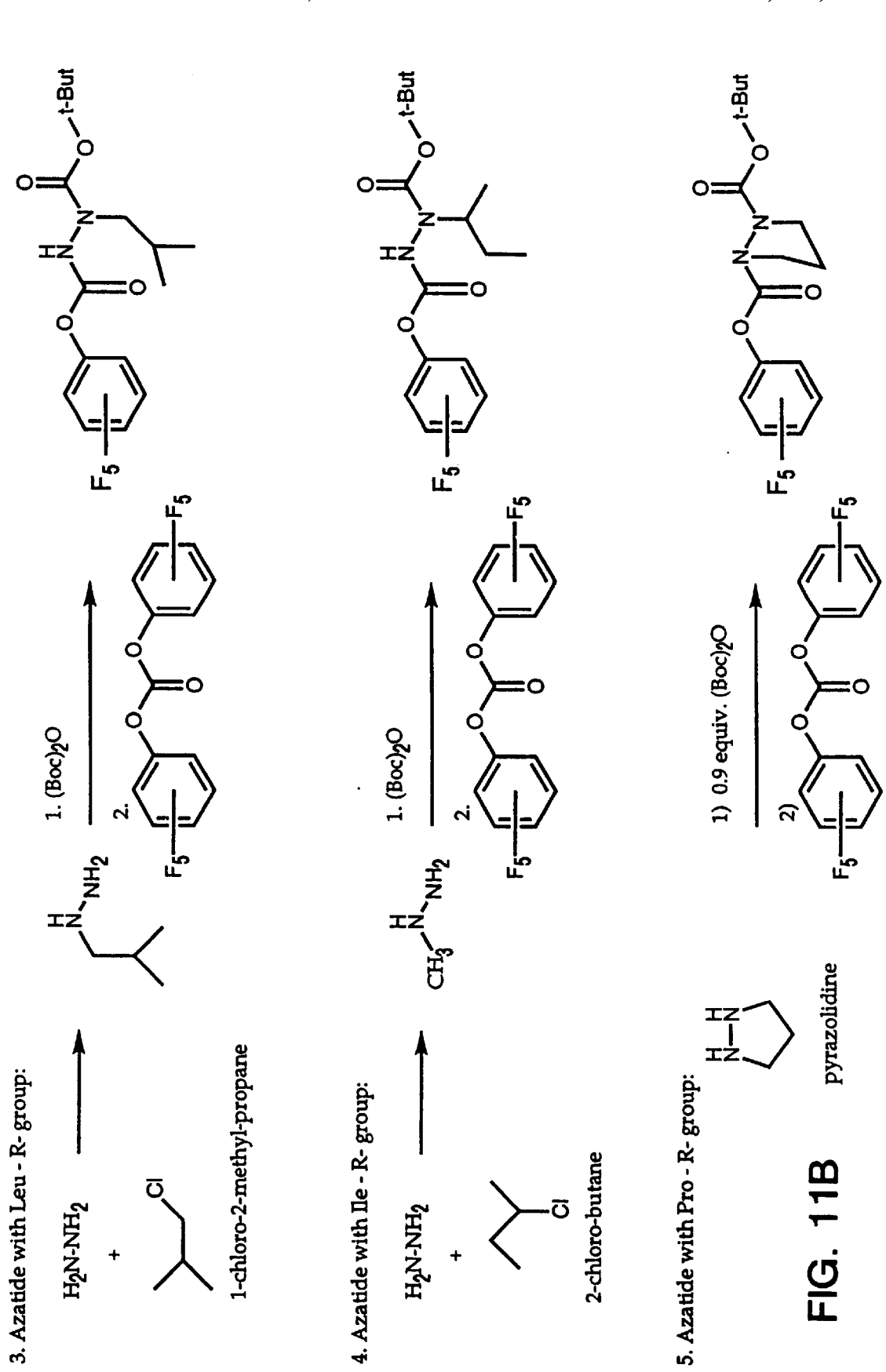

FIGS. 11A and 11B illustrate the synthesis of activated pentafluorophenyl carbamate-azetides for the common amino acids.

Figure 12A:
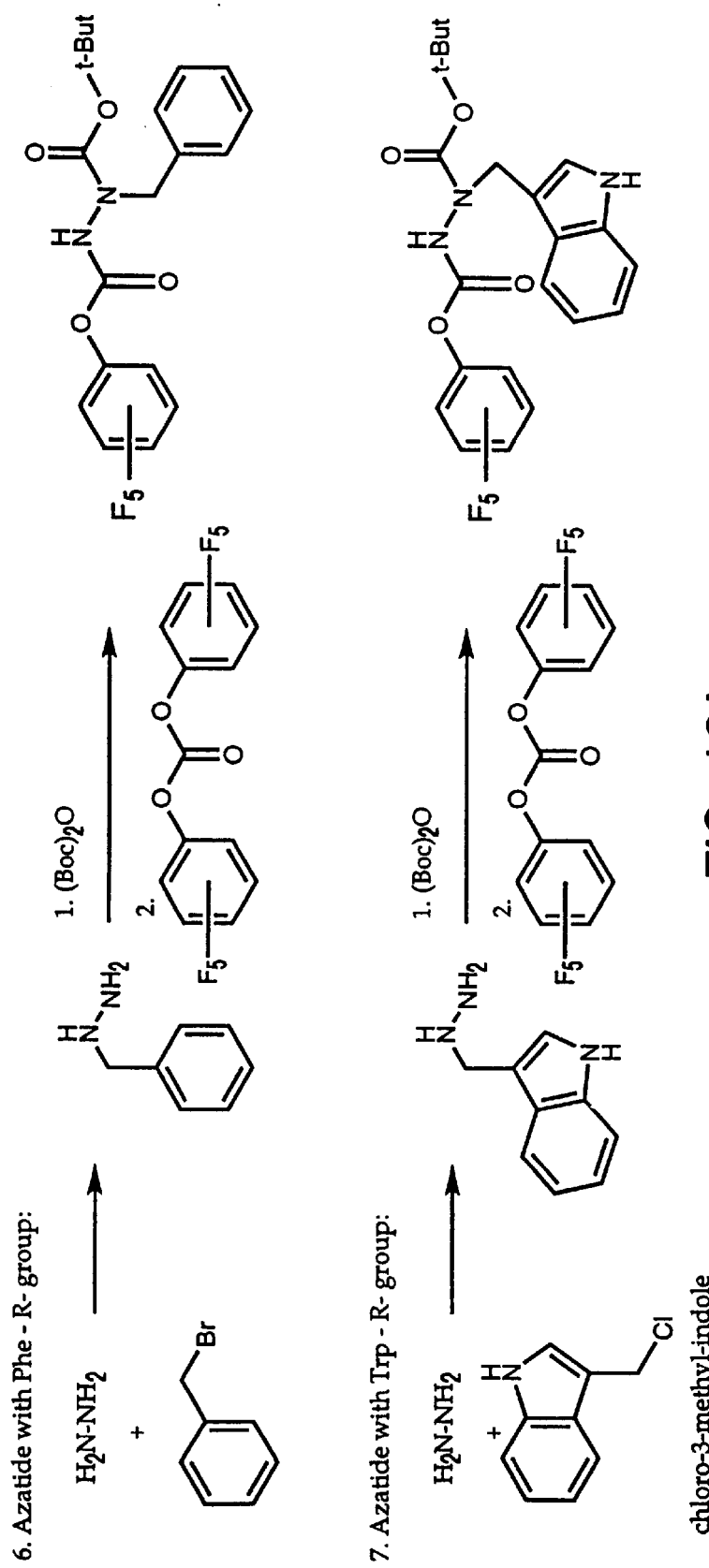

FIGS. 12A and 12B illustrate the synthesis of activated pentafluorophenyl carbamate-azetides for the common amino acids.

Figure 13A:
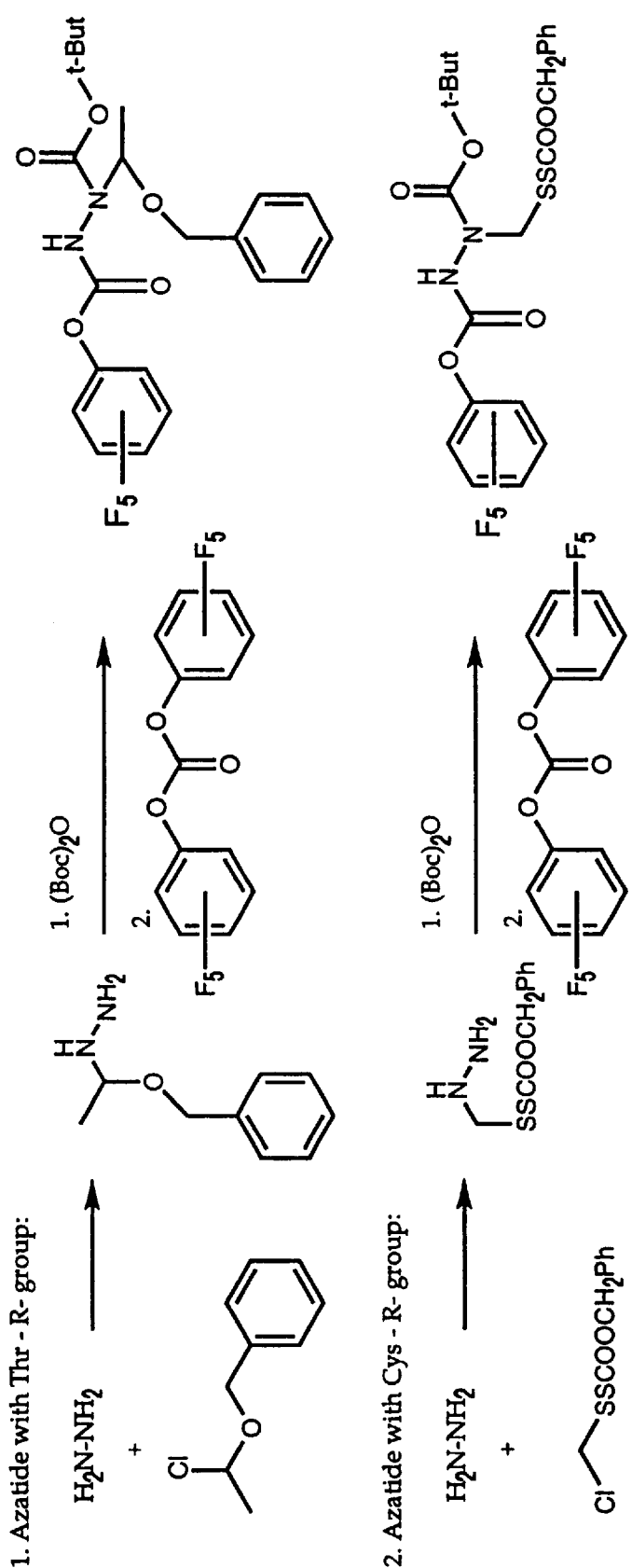

FIGS. 13A and 13B illustrate the synthesis of activated pentafluorophenyl carbamate-azetides for the common amino acids.

Figure 14A:
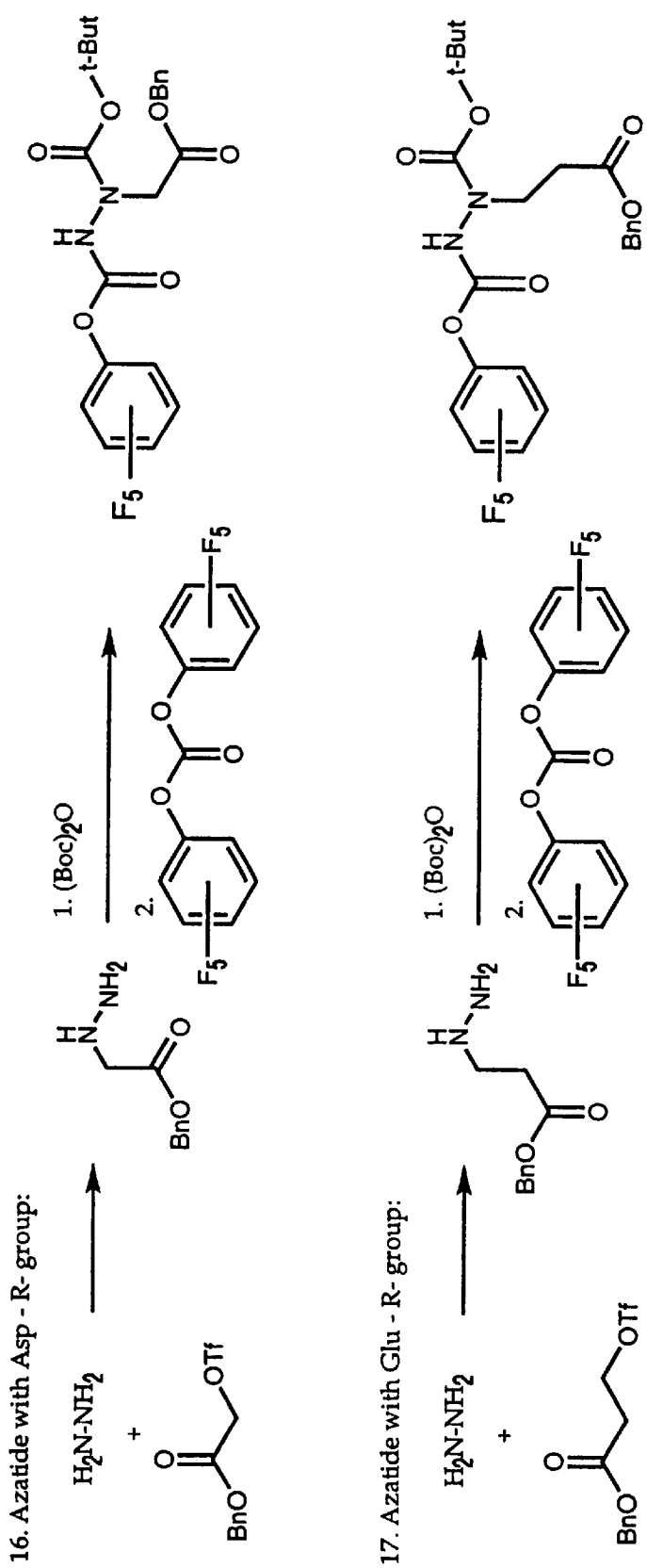

FIGS. 14A and 14B illustrate the synthesis of activated pentafluorophenyl carbamate-azetides for the common amino acids.

FIG. 15 illustrates activated pentafluorophenyl carbamate-azetides for the common amino acids.

FIG. 16 illustrates activated pentafluorophenyl carbamate-azetides for the common amino acids.

DETAILED DESCRIPTION OF THE INVENTION

The invention is directed to azatides and the design and general synthesis of oligoazatide mimetics. Thus, for the synthesis of oligoazatides, an alphabet of suitably protected aza-amino acid constituents are needed. The invention embodies a methodology to synthesize de novo Boc-protected alkylhydrazine monomers substituted with a variety of functional groups. Two principal routes are used in their syntheses (FIG. 2): (1) Reduction of Boc-protected hydrazones (Dutta et al. *J. Chem. Soc. Perkin Trans* 1 1975, 1712), derived from the reaction of Boc-carbazate with either an aldehyde or ketone (FIG. 2; equation 1). (2) Alkylation of hydrazine with an alkylhalide, followed by Boc-protection of the resulting alkylhydrazine (FIG. 2; equation 2) (Biel et al. *J. Am. Chem. Soc.* 1959, 81, 2805). The outgrowth of these methods is the transient protection of either the "amino or carboxy-terminal" functionality of the aza-amino acid and an ability to create a unique alphabet of α-aza-amino acid R-groups.

To convert these Boc-protected aza-amino acids into acylating agents that would allow stepwise chain lengthening, the hydrazine portion of the molecule had to be activated (FIG. 3). Activation of this moiety is a challenging problem since the Boc-alkylhydrazines are poorer nucleophiles than simple amines or amino acids. Consequently, we required a highly activated carbonyl synthon that would allow facile coupling of two Boc-protected aza-amino acids to form the azatide-linkage. Furthermore, this coupling reaction had to be controllable, such that symmetrical dimer formation could be mimimized. Our initial attempts to couple two aza-amino acids together using p-nitrophenyl chloroformate, carbonyldiimidazole, bis-(2,4-dinitrophenyl) carbonate, or trichloromethyl chlorofomate were unsuccessful, as they suffered from complicated side-reactions, poor reaction yields, and/or prolonged reaction time. We reasoned that these results were due to either the insufficient leaving ability of p-nitrophenol and imidazole, or steric hindrance of the o-nitro group in the case of bis-(2,4-dinitrophenyl) carbonate. To overcome these problems we opted to use bis-pentafluorophenyl carbonate 1 as the carbonyl activation element (Efimov et al. Nucleic Acids Research 1993, 21, 5337). Our decision to use this reagent was based on three factors. First, the pentafluorophenol functionality is a powerful electron-withdrawing group, while the fluoro substituents minimize steric problems. Second, the bis-pentafluorophenyl carbonate can be readily prepared from phosgene and a sodium pentafluorophenolate solution. Third, the compound is a highly crystalline solid which is easy to handle.

Figure 1:
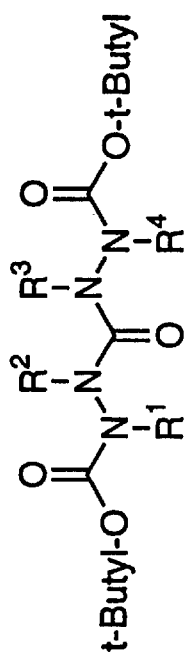
FIG. 1 shows a table which indicates yields of the preparation of various diazatides starting from 1-R- hydrazine carboxylic acid, 1,1-dimethylethyl ester wherein R ($R^1$, $R^2$, $R^3$ and $R^4$) is represented by the indicated functional groups.

Shown in (FIG. 3) are two solution phase routes to diazatides. In the first case, carbamate 2 is utilized for the coupling reaction. Thus, a Boc-protected aza-amino acid is added dropwise to 1 granting activation of the 1-R' hydrazinecarboxylic acid, 1,1-dimethylethyl ester. The activated complex formed, 2, is not isolated but instead immediately reacted via the addition of a second Boc-protected alkylhydrazine to complete the diazatide coupling. This coupling procedure provides diazatides in good yield with few side reactions in an acceptable reaction time. Results using this coupling method are summarized in (FIG. 1). From this table, it is evident that the coupling process is quite general, as both simple $Gly^a$-$Gly^a$ (superscript a refers to an aza-amino acid linkage) and sterically demanding ($Val^a$-$Val^a$) azatides can be synthesized in less than an hour. The latter result is extremely important as it dictates whether the stepwise coupling of aza-amino acids is feasible. Whereas coupling through activated 1-R' hydrazinecarboxylic acid, 1,1-dimethylethyl ester was successful, the coupling of activated 2-R' hydrazinecarboxylic acid, 1,1-dimethylethyl ester was not (FIG. 3). From these findings, we surmise that the activated complex is not carbamate 2, but rather the isocyanate 3 as follows:

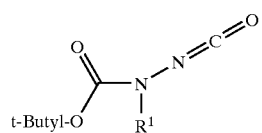

3

Findings reported by Abeles (Magrath et al. *J. Med. Chem.* 1992, 35, 4279) support this disclosure. For an activated 2-R' hydrazinecarboxylic acid, 1,1-dimethylethyl ester, the intermediate is untenable because of the carbamate's substitution pattern.

The techniques described above allow α-azatide chain building to be performed in an iterative manner.

To prepare a small well-defined α-azatide, we chose to use polymer-supported liquid phase synthesis (Geckeler et al. Advances in Polymer *Science*; Abe, A. et. al. Ed.; Springer-Verlag: Berlin, 1995, Vol. 121, p. 31). Liquid phase synthesis uses a soluble linear homopolymer [polyethylene glycol monomethyl ether (MeO-PEG)] which serves as a terminal protecting group for the compound to be synthesized. The essence of this technology is that it avoids a number of difficulties found in solid-phase synthesis and preserves the positive aspects of solution phase synthesis. We have demonstrated the advantages of using liquid phase synthesis through the construction of both peptide and small molecule combinatorial libraries (Han et al. *Proc. Natl. Acad. Sci. USA* 1995, 92, 6419).

A leucine-enkephalin peptide sequence, (YGGFL) (SEQ ID NO:1), was chosen as the first azatide mimetic to be synthesized. This pentamer was selected as the N-terminal sequence within this unit, (YGGF) (SEQ ID NO:2), is common to most natural opioid peptides (Meo et al. *Proc. Natl. Acad. Sci. USA* 1983, 80, 4084). The successful diazatide coupling procedure described in (FIG. 3) implies N-to-C-terminal construction of the azatide. A p-substituted benzyl ester spacer unit that would accommodate directional synthesis on MeO-PEG and withstand the rigors of Boc-chemistry was designed (12, FIG. 4). It was reasoned that 12 attached to MeO-PEG would be stable against acidolysis due to the presence of the para-benzoate substituent, and the oligoazatide could be liberated by catalytic hydrogenation generating a free amino group. Thus methyl p-(hydroxymethyl) benzoate was O-protected as the t-butyl ether by treatment with isobutylene and acid. Subsequent hydrolysis of the methyl ester with lithium hydroxide provided 12. Linker 12 was coupled to MeO-PEG with the aid of DCC/DMAP and upon deprotection with trifluoroacetic acid (TFA) gave the MeO-PEG-benzyl-OH (13) support ready for azatide synthesis. Synthesis of the azatide pentamer $Y^aG^aG^aF^aL^a$ was accomplished in a repetitive stepwise fashion as shown in (FIG. 4). Because of the unique physical properties of the MeO-PEG homopolymer each coupling/deprotection reaction could be purified by precipitation of the modified homopolymer. Furthermore MeO-PEG allows reaction progress to be conveniently monitored by either proton-NMR spectroscopy or the Kaiser ninhydrin test (Kaiser et al. Anal. Biochem. 1979, 34, 595). Based on our linker strategy, the pentamer and the benzyl protecting group of aza-tyrosine could be liberated in a single step using catalytic hydrogenation to give the Boc-protected pentamer (overall yield: 56.7% from 13). This compound was converted to the desired Leu-enkephalin azatide by treatment with trifluoroacetic acid (FIG. 4).

Tandem mass spectrometry (Hunt et al. *Proc. Natl. Acad. Sci. USA*. 1986, 83, 6233; Biemann et al. *Methods in Enzymology* 1990,193, 455), when coupled with any soft ionization method, has emerged as an important tool for the elucidation of sequences of peptides and nucleotides. We used this technique for the sequence determination of our azatide. Thus, the Leu-enkephalin azatide was subjected to ESI-tandem mass spectrum analysis. In the acidic matrix employed for ESI experiments, Leu-enkephalin azatide would exist as a $(M+H)^+$ ion with a proton located on the α-nitrogen atom of $Leu^a$ (i.e. the most basic residue). In the gas phase, $(M+H)^+$ ions undergo proton-transfer to other basic sites to allow charge delocalization. For an azatide, proton transfer would preferentially occur on the more basic tertiary amide nitrogens over the secondary amide nitrogens. The protonation of a tertiary amide nitrogen causes bond-cleavage between the α-nitrogen and carbonyl carbon to generate X- and A-type fragments (FIG. 6). When there is no preferential protonation between two secondary amide nitrogens such as in the urea-linkage involving the $Gly^a$ residues, cleavage is possible on either side of the carbonyl group. Conversely, Y- and B-type fragmentations of peptides results from protonation of amide nitrogens and hence cleavage of amide bonds (FIG. 6). This prediction was manifested in the collision-induced dissociation (CAD) pattern of Leu-enkephalin azatide 16 shown in (FIG. 7). The MS-MS of the $(M+H^+)$ ion at 517 produced daughter peaks at 403, 255,197 (A-type), 321, 263 (X-type) and MS-MS-MS on 403 $(M-Leu^a+H^+)$ gave grand-daughter peaks at 255, 197, 139 (A-type), 207, 149 (X-type), 239, 197, 123 (Y-type). Peaks at 297, 149, 107, 91 represent A-type fragments involving cleavage of side-chain of $Tyr^a$. Mass difference between homologous A-type ions corresponds to elements —CONHNR—. Predicted m/z values for $A_2$–$A_5$ fragments were obtained by sequentially adding the incremental masses of $Gly^a$, $Gly^a$, $Phe^a$, and $Leu^a$ to that for $A_1$ at 139. A similar arguement can be made for X-type and Y-type fragments, confirming the $Tyr^a$-$Gly^a$-$Gly^a$-$Phe^a$-$Leu^a$ sequence of Leu-enkephalin azatide.

The azatide oligomer sequence synthesized, (Tyr$^a$-Gly$^a$-Gly$^a$-Phe$^a$-Leu$^a$), provided a chance to assess any biological activity that this azatide biopolymer sequence may posses (vide supra). Monoclonal antibody 3-E7 was raised by Meo et al. against the antigen β-endorphin and, like the δ-opioid receptor, recognizes the N-terminal portion of the protein (Meo et al. *Proc. Natl. Acad. Sci. USA* 1983, 80, 4084). The antibody also binds tightly to [Leu$^5$]-enkephalin [Tyr-Gly-Gly-Phe-Leu] (SEQ ID NO:1), ($K_d$=7.1 nM) and a variety of related opioid peptides (Cwirla et al. *Proc. Natl. Acad. Sci. USA* 1990, 87, 6378) A competition ELISA method was used to investigate if the Tyr$^a$-Gly$^a$-Gly$^a$- Phe$^a$-Leu$^a$ sequence could bind to IgG 3-E7 (Han et al. *Proc. Natl. Acad. Sci. USA* 1995, 92, 6419). At 1 mM the azatide pentamer showed no propensity to compete with the natural peptide for 3-E7. While this result at first glance appears to be disappointing it was not completely unexpected. The bound conformation(s) of enkephalin have been studied extensively for over the past 15 years (Garner et al. *Tetrahedron* 1993, 49, 3433). While the exact bioactive conformation of this peptide remains shrouded, it is thought that the active form of this peptide resides in some sort of a 9-turn (Bradbury et al. *Nature* 1976, 260, 165; Lowe et al. *Proc. Natl. Acad. Sci. USA* 1978, 75, 7; Manavalan et al. *Int. J. Pept. Protein Res.* 1981, 18, 256). This being based on x-ray crystallographic data which showed that the glycine residues at the second and third position of enkephalin force a type I'4→1 β-turn (Smith et al. *Science* 1978, 199, 1214; Ishida et al. *Biochem. J.* 1984, 218, 677). Although we have yet to obtain an x-ray structure on 16, physiochemical data does exist on diacyl hydrazines (Olivato et al. J. Chem. Soc., Perkin Trans. II 1983, 1053; Graybill et al. *Bioorg. & Medicinal Chem. Lett.* 1992, 2, 1375). Simple unsubstituted diacyl hydrazine's (i.e. glycine azatides) contain a dihedral (φ) angle of approximately −175 degrees. While N-substituted (i.e. all other azatides) possess a dihedral (φ) angle of approximately −110 degrees. Taken as a whole this data suggests that 16 should adopt a more extended conformation within the critical glycine region. In essence then this azatide oligomer would have difficulty in achieving the orientation displayed by the antigenic determinant (Tyr-Gly-Gly-Phe-Leu) (SEQ ID NO:1) that elicited IgG 3-E7. The outcome being that 16 is non-ligand for 3-E7.

SYNTHETIC PROTOCALS

General $^1$H and $^{13}$C nmr spectra were recorded either on a Bruker AM-250, a Bruker AMX-400 or a Bruker AMX-500 spectrometer. Residual protic solvent CHCl$_3$ ($δ_H$=7.26 ppm, $δ^c$=77.0), d$_4$-methanol ($δ_H$=3.30 ppm, $δ_C$=49.0) and D$_2$O ($δ_H$=4.80 ppm, $δ_C$ (of $\underline{C}$H$_3$CN)=1.7 ppm) or TMS ($δ_H$=0.00 ppm) were used as internal reference. Coupling constants were measured in Hertz (Hz). HRMS were recorded using FAB method in a m-nitrobenzylalcohol (NBA) matrix doped with NaI or CsI. Infra-red spectra were recorded on a Perkin-Elmer FTIR 1620 spectrometer. Enantiomeric excess was determined by HPLC using a Daicel Chemical Industries CHIRALPAK AD column. Optical rotations were measured with an Optical Activity AA-1000 polarimeter. Melting points were taken on a Thomas Hoover capillary melting point apparatus and are uncorrected. Column chromatography was performed on Merck Kieselgel 60 (230–400 mesh). Analytical thin layer chromatography was performed using pre-coated glass-backed plates (Merck Kieselgel F$_{254}$) and visualized by cerium molybdophosphate or ninhydrin. Diethyl ether, tetrahydrofuran (THF) and toluene (PhCH$_3$) were distilled from sodium-benzophenone ketyl, dichloromethane (DCM) and acetonitrile from calcium hydride. Other solvents and reagents were purified by standard procedures if necessary. The optical rotations wre measured with a JASCO DIP-1000KUY automatic digital polarimeter. $^1$H and $^{13}$C-NMR spectra were measured with a JEOL EX 270 and/or a 500 FT-NMR spectrometer and chemical shifts were given on a d (ppm) scale with tetramethylsilane as an internal standard. The FAB-MS were measured with a JEOL DX-300 and/or SX102A spectrometer. MALDI-TOF Mass was measured under the condition: Positive mode, 6 kV, Reflectron with gentisc acid as the matrix by Kratos Kompact (Shimazu, MALDI-III). TLC was performed on precoated Kieselgel 60 F$_{254}$ plates (Merck). Column chromatography was carried out on Kieselgel 60 (70–230 mesh and 230–400 mesh) and MCI gel CHP-20P (Mitsubishi Chemical, Ind.). Polyethylene glycol monomethyl ether (MeO-PEG, MW.=5000) was purchased from Aldrich and was dried over P$_2$O$_5$ under vacuum before use. Boc-protected methylhydrazines, isopropylhydrazines, isobutylhydrazines, benzylhydrazines, p-(O-benzyl) hydroxybenzylhydrazines, and pentafluorophenyl carbonate were prepared according to literature procedures (DMAP is 4-N-dimethylaminopyridine).

General Solution Phase Diazatide Coupling Procedure as Illustrated in FIG. 3, Equation 1:

To a stirred solution of pentafluorophenyl carbonate 1 (50.0 mg, 13.0 mmol; synthesis vida infra) in methylene chloride (5 ml) over a period of 20 min, a solution of 1-(N-Boc)-alkylhydrazine (1 eq; synthesis vida infra) and DMAP (1 eq) in methylene chloride (2 ml) is added dropwise to form compound 2. Upon completion of the addition, a solution of 2-(N-Boc)-alkylhydrazine (1 eq; synthesis vida infra) and DMAP (1 eq) in methylene chloride (2 ml) are added. The resulting mixture was stirred for 30 min at room temperature. Removal of solvent and flash chromatography (Still et al. *J. Org. Chem.* 1978, 43, 2923) gives the desired unsymmetrical diazatide.

Boc-Gly$^a$-Gly$^a$-Boc Case:
$^1$H-NMR (300 MHz, CDCl$_3$) δ 1.35 (s, 18H), 7.33 (broad s, 2H), 7.77 (s, 2H); $^{13}$C-NMR (75 MHz, CDCl$_3$) δ 27.9, 81.3, 156.2; 157.1; HRMS (FAB) calcd for [C$_{11}$H$_{22}$N$_4$O$_5$+Cs$^+$] 423.0645, found 423.0655.

Boc-Ala$^a$-Ala$^a$-Boc Case (Symmetrical):
$^1$H-NMR (300 MHz, CDCl$_3$) δ 1.42 (s, 18H), 3.09 (s, 6H), 7.43 (s, 2H); $^{13}$C-NMR (75 MHz, CDCl$_3$) δ 28.1, 38.3, 81.5, 156.1, 157.0; HRMS (FAB) calcd for [C$_{13}$H$_{26}$N$_4$O$_5$+Cs$^+$] 451.0958, found 451.0976.

Boc-Ala$^a$-Ala$^a$-Boc Case:
$^1$H-NMR (300 MHz, CDCl$_3$) δ 1.43 (s, 9H), 1.45 (s, 9H), 3.08 (s, 3H), 3.09 (s, 3H), 6.45 (broad s, 1H), 7.05 & 7.62 (broad s, 1H); $^{13}$C-NMR (75 MHz, CDCl$_3$) δ 28.2, 28.3, 37.9, 81.2, 81.4, 155.4, 156.6, 156.8; HRMS (FAB) calcd for [C$_{11}$H$_{22}$N$_4$O$_5$+Cs$^+$] 451.0958, found 451.0965.

Boc-Ala$^a$-Phe$^a$-Boc:
$^1$H-NMR (300 MHz, CDCl$_3$) δ 1.37 (s, 9H), 1.41 (s, 9H), 3.1 (s, 3H), 4.50 (broad s, 2H), 6.10 & 6.59 (broad s, 1H), 7.22 (m, 5H), 7.37 & 7.55 (broad s, 1H); $^{13}$C-NMR (75 MHz, CDCl$_3$) δ 27.8, 28.2, 38.5, 54.3, 81.5, 81.6, 127.3, 128.3, 128.6, 137.3, 155.5, 156.4, 156.5; HRMS (FAB) calcd for [C$_{19}$H$_{30}$N$_4$O$_5$+CS$^+$] 527.1271, found 527.1289.

Boc-Ala$^a$-Leu$^a$-Boc:
$^1$H-NMR (300 MHz, CDCl$_3$) δ 0.90 (d, J=7 Hz, 6H), 1.40 (s, 9H), 1.45 (s, 9H), 1.84 (m, 1H), 3.07 (s, 3H), 3.35 (broad s, 2H), 6.30 & 6.56 (broad s, 1H), 7.20 & 7.36 (broad s, 1H); $^{13}$C-NMR (75 MHz, CDCl$_3$) δ 19.9, 26.3, 28.1, 28.3, 38.0, 55.7, 81.1, 82.0, 154.5, 156.1, 157,6; HRMS (FAB) calcd for [C$_{16}$H$_{32}$N$_4$O$_5$+Cs$^+$] 493.1427, found 493.1447.

Boc-Leu$^a$-Leu$^a$-Boc:

$^1$H-NMR (300 MHz, CDCl$_3$) δ 0.88 (d, J=7 Hz, 6H), 0.90 (d, J=7 Hz, 6H), 1.42 (s, 9H), 1.46 (s, 9H), 1.86 (m, 2H), 3.27 (broad s, 4H), 6.33 & 6.57 (broad s, 1H), 7.11 & 7.23 (broad s, 1H); $^{13}$C-NMR (75 MHz, CDCl$_3$) δ 20.4, 20.4, 27.6, 27.8, 28.5, 28.6, 56.7, 59.5, 81.8, 82.3, 156.3, 156.5, 158.1; HRMS (FAB) calcd for (C$_{19}$H$_{38}$N$_4$O$_5$+Cs$^+$) 535.1897, found 535.1881.

Boc-Val$^a$-Val$^a$-Boc:

Melting point was 101–102° C.; $^1$H-NMR (300 MHz, CDCl$_3$) δ 1.09 (broad s, 12H), 1.40 (s, 9H), 1.45 (s, 9H), 4.32 (broad s, 1H), 4.61(m, 2H), 6.27 (broad s, 1H), 6.79 (broad s, 1H); 13C-NMR (75 MHz, CDCl$_3$) δ 19.3, 19.8, 28.0, 28.3, 48.4, 48.6, 81.0, 81.6, 157.1, 157.4, 157.9; HRMS (FAB) calcd for [C$_{17}$H$_{34}$N$_4$O$_5$+Cs$^+$] 507.1584, found 507.1599.

Linker Preparation

Methyl p-(O-t-Butyl)hydroxymethylbenzoate (FIG. 4; Intermediate to 12):

Isobutylene was liquidified in a sealed bottle at −78° C. A solution of sulfuric acid (0.5 ml) and methyl p-hydroxymethylbenzoate (2.00 g, 12.0 mmol) in dry ethyl ether (20 ml) was added to the isobutylene solution (8 ml) at −78° C. and stirred overnight at room temperature. The resulting mixture was cooled to 4° C., then ice-cooled water was added. The ether layer was dried over magnesium sulfate and evaporated to give the desired product as a white solid (2.59 g, 96.8%): m.p. 34–36° C.; $^1$H NMR (300 MHz, CDCl$_3$) δ 1.29 (s, 9H), 3.89 (s, 3H), 4.49 (s, 2H), 7.40 (d, J=6.7 Hz, 2H), 7.98 (d, J=6.7 Hz, 2H); $^{13}$C-NMR (75 MHz, CDCl$_3$) δ 27.5, 51.8, 63.4, 73.6, 126.8, 128.7, 129.5; HRMS (FAB) calcd for [C$_{13}$H$_8$O$_5$+Cs$^+$] 355.0310, found 355.0323.

Synthesis of p-(O-Butyl)hydroxymethylbenzoic Acid (12; FIG. 4):

Methyl p-(O-t-butyl)hydroxymethylbenzoate (2.02 g, 9.10 mmol) was dissolved in a 0.8 M LiOH solution in methanol and H$_2$O (34 ml; methanol: H$_2$O, 3:1). The reaction mixture was stirred until the starting material disappeared as judged by TLC (methylene chloride: ethyl ether= 9:1). The reaction mixture was acidified by the addition of 1N-HCl and extracted with methylene chloride. The methylene chloride layer was dried over magnesium sulfate and then evaporated to give the desired product as a white solid (1.72 g, 90.9%): m.p. 147–149° C.; $^1$H NMR (300 MHz, CDCl$_3$) δ 1.39 (s, 9H), 4.50 (s, 2H), 7.42 (d, J=6.8 Hz, 2H), 8.06 (d, J=6.8 Hz, 2H); $^{13}$C-NMR (75 MHz, CDCl$_3$) δ 27.6, 63.6, 73.9, 127.0, 128.0, 130.3, 146.4, 171.8; HRMS (FAB) calcd for [C$_{12}$H$_{16}$O$_3$+Na$^+$] 231.0997, Found 231.0986.

Synthesis of MeO-PEG-Linker-Y$^a$G$^a$G$^a$F$^a$L$^a$

Attachment of p-(O-Butyl)hydroxymethylbenzoic Acid (12) to MeO-PEG; [MeO-PEG-benzyl-OH (13); as Illustrated in FIG. 4]

Compound 12 (125 mg, 601 μmol), MeO-PEG (1.00 g, 200 μmol), and DMAP (611 μg, 50.0 μmol) were dissolved in methylene chloride (10 ml), and DCC (124 mg, 601 μmol; dicyclohexylchlorodiimide) was added. The resulting mixture was stirred for 12 h. The precipitated urea was filtered through celite. Diethyl ether was slowly added to the filtrate in order to precipitate the polymer. The polymer precipitate was washed with cold absolute ethanol and ether, and dried over P$_2$O$_5$ under vacuum. This solid was dissolved in trifluoroacetic acid, and the resulting solution was stirred for 9 min at room temperature. The whole reaction mixture was poured onto an ice-cold diethyl ether solution with vigorous stirring. The precipitate was collected, washed with cold absolute ethanol and diethyl ether, and dried over P$_2$O$_5$ under vacuum (935 mg, 91.1%): $^1$H NMR (300 MHz, CD$_3$OD) δ 4.45 (t, J=7 Hz, 2H), 4.71 (s, 2H), 7.41 (d, J=7Hz, 2H), 7.98 (d, J=7 Hz, 2H).

Construction of (O-Benzyl)Tyr$^a$-Gly$^a$-Gly$^a$-Phe$^a$-Leu$^a$-Boc on (13 to Form 14 and 15; FIG. 4):

A mixture of 13 (195 mg, 38.0 μmol), pentafluorophenyl carbamate of Boc-[p-(O-benzyl)hydroxybenzyl]hydrazine (102 mg, 5 eq), and DMAP (23.2 mg, 5 eq) in methylene chloride (5 ml) was stirred for 24 h at room temperature. Diethyl ether was slowly added to this mixture to precipitate the polymer product 14. The polymer product was washed with absolute ethanol and diethyl ether, and dried over P$_2$O$_5$ under vacuum: $^1$H NMR (300 MHz, CD$_3$OD) δ 1.40 (s, 9H), 4.45 (2H), 4.55 (2H), 5.00 (2H), 5.15 (2H), 6.55 (1H), 6.88 (2H), 7.15 (2H), 7.38 (7H), 8.00 (2H). The polymer 14 was dissolved in TFA/methylene chloride, and stirred for 30 min to remove the Boc-group. Precipitation with ether, a separate wash with absolute ethanol and diethyl ether followed by drying over P$_2$O$_5$ under vacuum gave the trifluoro acetate salt of [p-(O-benzyl)hydroxybenzyl]Tyr$^a$-O-benzyl-PEG-OMe. This salt was dissolved in methylene chloride and neutralized with diisopropylethylamine (DIPEA, 1 eq). To the resulting mixture was added the pentafluorophenyl carbamate of Boc-carbazate (5 eq) and DMAP (5 eq). The reaction mixture was stirred for 4 h. Precipitation with diethyl ether followed by washing with absolute ethanol and diethyl ether, then drying over P$_2$O$_5$ under vacuum gave the product, Boc-Gly$^a$-(O-benzyl)-Tyr$^a$-O-benzyl-PEG-OMe. Repetition of this cycle of deprotection, neutralization, and coupling with Gly$^a$, Phe$^a$, and Leu$^a$ produced the Leu-enkephalin azatide 15 (137 mg, 62.4% from 13): $^1$H NMR (300 MHz, CD$_3$OD) δ 0.87 (6H), 1.42 (9H), 1.91 (1H), 4.43 (2H), 4.96 (2H), 5.12 (2H), 6.83 (2H), 7.13 (2H), 7.37 (7H), 7.95 (2H). The mutiplicity of peaks is not described due to the peak broadening.

Synthesis of Tyr$^a$-Gly$^a$-Gly$^a$-Phe$^a$-Leu$^a$-Boc (Protected Intermediate of 16; FIG. 4):

Compound 15 (137 mg, 23.7 μmol) was hydrogenated with 10% Pd/C (100 mg) in methanol (5 ml) under a balloon containing one atmosphere of hydrogen for 4 h. All volatiles were removed in vacuo and the residue was extracted with absolute ethanol. This ethanol solution was concentrated and purified by preparative thin layer chromatography. The desired material was observed as a single band R$_f$=0.4 (13.25 mg, 90.7%, TLC solvent methylene chloride:methanol=9:1): $^1$H NMR (300 MHz, CD$_3$OD) δ 0.93 (d, J=7 Hz, 6H), 1.43 (s, 9H), 1.47 (s, 9H), 1.95 (m, 1H), 3.27 (broad s, 2H), 4.17 & 5.19 (broad s, 2H), 4.50 (broad s, 2H), 6.76 (d, J=6.7 Hz, 2H), 7.12 (d, J=6.7 Hz, 2H), 7.33 (m, 5H); m/z (ESI, positive) 639 (M+Na)$^+$, 617 (M+1)$^+$.

Synthesis of Tyr$^a$-Gly$^a$-Gly$^a$-Phe$^a$-Leu$^a$.2CP$_3$COOH (16; FIG. 4):

Tyr$^a$-Gly$^a$-Gly$^a$-Phe$^a$-Leu$^a$-Boc (13.25 mg, 21.5 μmol) was dissolved in TFA/methylene chloride (5 ml) and stirred for 30 min. All volatiles were removed in vacuo to give the desired product as a white hygroscopic solid (16.0 mg, 100%): $^1$H NMR (300 MHz, CD$_3$OD) δ 1.05 (d, J=6.7 Hz, 6H), 2.09 (m, $^1$H), 3.07 (broad s, 2H), 4.22 & 5.26 (broad s, 2H), 4.65 (broad s, 2H), 6.77 (d, J=6.8 Hz, 2H), 7.17 (d, J=6.8 Hz, 2H), 7.35 (m, 5H); m/z (ESI, positive) 539 (M+Na)$^+$, 517 (M+1)$^+$.

Azatide (16) Competition ELISA for Anti-β-Endorphin Monoclonal Antibody.

Each well of a Costar 96-well plate that was used in the competition was initially coated with 25 μl of Tyr-Gly-Gly-Phe-Leu-CO—NH—(CH$_2$)$_2$—NH—CO—(CH$_2$)$_2$-SS-BSA (SEQ ID NO:3) (5–20 mg/ml) in 60 mM sodium bicarbonate/30 mM sodium carbonate, pH 9.3, overnight. The wells were washed ten times with deionized water and blocked with 100 ul of 3% BSA (all in PBS with 0.5% Tween) to prevent nonspecific adsorption. After incubating for 30 min at 37° C. in moist chamber, the 3% BSA was then shaken out and 25 μl of 3% BSA and 25 μl of 16 (competing antigen) were added to first well and serially diluted across plate; the same process was then continued in first well of second row. Well 12 was used as the positive control. The anti-β-endorphin antibody (diluted in 1% BSA/PBS with 0.50 Tween) was added to each well (25 ul) and the plate was incubated at 37° C. for 2 hours. The plate was washed 20 times with deionized water, and 25 μl of a 1:1000 dilution of goat anti-mouse IgG glucose oxidase conjugate (Cappel) in 1% BSA was added to each well and the plate was incubated at 37° C. for 1 hour. The plates were washed 20 times with deionized water and bound antibody was detected by the addition of 50 μl of developing agent [0.6 ml 20% glucose, 40 μl 92 mM 2,2'-azinobis(3-ethylbenzthiazolinesulfonate), and 40 μl of 25 μM horseradish peroxidase in 5 ml of phosphate buffer, pH 6.0] to each well. Thirty minutes later the plates were read at 405 nm.

Synthesis of Protecting Group: Bispentafluorophenol Carbonate (1) as Shown in FIG. 3:

Pentafluorphenol (0.27 mol.; commercially available from Aldrich chemical) was dissolved in 0.5 Molar KOH and cooled to 0° C. Phosgene was then passed through this solution with vigorous mixing. The pH of the reaction mixture was controlled to be no less than 6.0. Sometimes the carbonate crystallized from solution, but more often an oily precipitate forme. Next, the reaction mixture was kept at 0° C. overnight. The solidified residue was filtered off, washed with water and dissolved in chloroform. The solution was dried over anhydrous sodium sulfate, filtered and evaporated. The crude crystalline product, with a strong, chloroformate-like odor from an impurity, was recrystallized from hexane. The yield was approximately 75%, starting with 55 grams pentafluorophenol.

General Synthesis of Compound 12 (FIGS. 4 and 8):

To a solution of methyl 4-(hydroxymethyl)benzoate (2.0 g, 12mmol, 1.0 equivalent, Aldrich) in 0.10 Molar diethylether, was bubbled 8 mL of isobutylene (2-methylpropene, commercially available from Aldrich) at −78° C. Next, 10 drops of sulfuric acid were added and the mixture was allowed to stir overnight. The reaction mixture was diluted with ether (25 mL), quenched with sodium bicarbonate (10 mL), washed with water (10 mL), condensed and dried over magnesium sulfate. The product can be purified by flash chromatography or distillation. The product is next exposed to 5 equivalents of LiOH·H$_2$O in a 3:1 mixture of methanol water (3 Molar). The mixture is allowed to stir for 2 hours at 25° C. and then is extracted with ether and acidified with 1 mL of HCl. The precipitate is collected on a glass filter and can be further purified by flash chromatography or crystallization.

Synthesis of compound 13 (FIG. 8):

To a solution of (MeO-PEG-OH, n=5000 MW, commercially available from Sigma Company) in 17 mM of methylene chloride at 250° C., is added 3.0 equivalents of compound 12, 3.0 equivalents of 1,3 dicyclohexyl carbodiimide (DCC) and 0.75 equivalents of 4-DMAP (4-dimethylaminopyridine). The reaction mixture is allowed to stir overnight. Next, the mixture is exposed to 3.0 equivalents of trifluoroacetic acid (TFA) and allowed to stir an additional 11 minutes at 25° C. The mixture is then poured into ice-cold ether (approximately 17 mM) to precipitate the PEG and then washed with cold ether and ethanol fractions. The final product can be further purified by crystallization from hot ethanol.

First Coupling of the Activated Azacarbamate Addition Molecule to the PEG Support (FIG. 8): Synthesis of Compound 17 (Library of Compounds With Chain Length 1):

To 1.0 equivalent of the PEG support (compound 13) in 17 mM methylene chloride at 25° C. (n-reaction vessels; wherein $1 \leq n \leq 100$), is added 5.0 equivalents of the activated azacarbamate (addition molecule-activated azacarbamate residues synthesized infra wherein $R_x$ is selected from the group consisting of hydrogen, methyl, isobutyl, isopropyl, benzyl, and the side chain radical of the following amino acids: Ala, Arg, Asn, Asp, Asx, Cys, Gln, Glu, Glx, Gly, His, Ile, Leu, Lys, Met, Phe, Pro, Ser, Thr, Trp, Tyr and Val.-combinatorial strategy in FIG. 8; the "n"th-addition molecule is added seperately to the "n"th reaction vessel which contains the PEG support) and 5.1 equivalents of 4-dimethylaminopyridine (4-DMAP; added to n reaction vessels). In each vessel, the reaction mixture is then allowed to stir for 24 hours and is next precipitated with the addition of ether (17 mM diethyl ether). The product is then further purified by washing with ether (1×) and crystallizing in cold ethanol (1×). ⅓ of the products of each "n" reaction vessels are saved and the remainer ⅔ of products are recombined and mixed into a single reaction vessel to form a library of nascent protected compounds with chain length 1 (compound 17).

Synthesis of Compound 18: Removal of Boc group (FIG. 8):

1.0 gram of compound 18 is exposed to a 10% trifluoroacetic acid/ methylene chloride solution (10 mL, 1:1 TFA/ methylene chloride) and allowed to stir at 25° C. for 1 hour. The reaction mixture is next precipitated with the addition of ether (17 mM diethyl ether). The product is then further purified by washing with ether (1×) and can be crystallized from ethanol (1×).

Second Coupling of the Activated Azacarbamate Addition Molecule to the PEG Support (FIG. 9): Synthesis of Compound 19 (Library of Compounds With Chain Length 2):

To 1.0 equivalent of the compound 18 in 17 mM methylene chloride at 25° C. (n-reaction vessels; wherein $1 \leq n \leq 100$), is added 5.0 equivalents of the activated azacarbamate (addition molecule-activated azacarbamate residues synthesized infra wherein $R_x$ is selected from the group consisting of hydrogen, methyl, isobutyl, isopropyl, benzyl, and the side chain radical of the following amino acids: Ala, Arg, Asn, Asp, Asx, Cys, Gln, Glu, Glx, Gly, His, Ile, Leu, Lys, Met, Phe, Pro, Ser, Thr, Trp, Tyr and Val combinatorial strategy in FIG. 9; the "n"th-addition molecule is added seperately to the "n"th reaction vessel which contains compound 18) and 5.1 equivalents of 4-dimethylamino pyridine (4-DMAP) is added to each of the n reaction vessels. In each vessel, the reaction mixture is then allowed to stir for 24 hours and is next precipitated with the addition of ether (17 mM diethyl ether). The product is then further purified by washing with ether (1×) and crystallizing in cold ethanol (1×). ⅓ of the products of each "n" reaction vessels are saved and the remainer ⅔ of products are recombined and mixed into a single reaction vessel to form a library of nascent protected compounds with chain length 2 (compound 19).

Synthesis of Compound 7: Removal of Boc group (FIG. 9):

1.0 gram of compound 19 is exposed to a 10% trifluoroacetic acid/ methylene chloride solution (10 mL, 1:1 TFA/ methylene chloride) and allowed to stir at 25° C. for 1 hour. The reaction mixture is next precipitated with the addition of ether (17 mM diethyl ether). The product is then further purified by washing with ether (1×) and can be crystallized from ethanol (1×).

Compound 22 is formed from an iterative cycle of steps 1–3 as outlined below and illustrated in FIG. 10:

Step 1: 'nth' Coupling of the Activated Azacarbamate to the PEG Support (as Illustrated in FIG. 10):

To 1.0 equivalent of the nascent deprotected chain of length 2 (compound 20) in 17 mM methylene chloride at 25° C. (n-reaction vessels; wherein $1 \leq n \leq 100$), is added 5.0 equivalents of the activated azacarbamate (see boxed addition molecule-activated azacarbamate residues synthesized infra wherein $R_x$ is selected from the group consisting of hydrogen, methyl, isobutyl, isopropyl, benzyl, and the side chain radical of the following amino acids: Ala, Arg, Asn, Asp, Asx, Cys, Gln, Glu, Glx, Gly, His, Ile, Leu, Lys, Met, Phe, Pro, Ser, Thr, Trp, Tyr and Val- combinatorial strategy in FIG. 10; the "n"th-addition molecule is added seperately to the "n"th reaction vessel which contains the PEG support) and 5.1 equivalents of 4-dimethylaminopyridine (4-DMAP; added to n reaction vessels). In each vessel, the reaction mixture is then allowed to stir for 24 hours and is next precipitated with the addition of ether (17 mM diethyl ether). The product is then further purified by washing with ether (1×) and crystallizing in cold ethanol (1×). ⅓ of the products of each "n" reaction vessels are saved and the remainer ⅔ of products are recombined and mixed into a single reaction vessel to form a library of nascent protected compounds with chain length n.

Step 2: 'nth' removal of Boc group (FIG. 10) 1.0 gram of the azatide polymer formed in step 1 is exposed to a 10% trifluoroacetic acid/ methylene chloride solution (10 mL, 1:1 TFA/ methylene chloride) and allowed to stir at 25° C. for 1 hour. The reaction mixture is next precipitated with the addition of ether (17 mM diethyl ether). The product is then further purified by washing with ether (1×) and can be crystallized from ethanol (1×).

Step 3: Repeat Steps i–ii as Desired:

Steps i–ii (supra) may be reiterated as many times as desired to create azatide polymers wherein $1 \leq n \leq 100$.

Synthesis of Compound 22: Final Deprotection Step (FIG. 10):

This step removes the aza-peptide from the PEG support and additionally removes the benzyl, benzyl ester, 9-fluorenylmethyl and S-sulfenylthiocarbonate protecting groups: To 1.0 gram of azatide polymer in 10 mL methanol at 25° C. is added 200 mg of 10% Pd/C. The reaction mixture is capped with a hydrogen balloon and allowed to stir overnight. The product is washed with ether, filtered and condensed. Further purification can be achieved by standard chromatographic methodologies for small azatides or crystallization for large polymers.

Removal of the remaining t-But protecting group: 1.0 gram of azatide polymer is exposed to a 10% trifluoroacetic acid/ methylene chloride solution (10 mL, 1:1 TFA/ methylene chloride) and allowed to stir at 25° C. for 1 hour. The product is washed with ether, washed with sodium bicarbonate, dried over sodium sulfate and condensed. Further purification can be achieved by standard chromatographic methodologies for small peptides.

Synthesis of Azatide Residue With Ala-R-group (FIG. 11; Equation 1):

A solution of 0.098 mole of methyl-iodide in 0.98 Molar of ethanol was added over a period of 1 hour to a refluxing solution of 0.51 mol of 85% hydrazine hydrate (commercially available from Aldrich company) in 2.55 Molar of ethanol. After a reflux period of 6 hours, the ethanol was removed by distillation. The residue was extracted with ether, the ethereal extracts dried with potassium carbonate and filtered. The crude base, 1.0 equivalent, was next exposed to 1.1 equivalents of di-tert-butyl dicarbonate (commercially available from Aldrich company) in 0.1 Molar methylene chloride and then stirred overnight at 25° C. The solvent was next removed by distillation and the remaining residue was extracted with ether, washed in water (1×) and dried over potassium carbonate and filtered. Product can then be purified by flash chromatography using a methylene chloride:ether/petroleum ether gradient.

Formation of the activated azacarbamate: 1.0 equivalent of the above synthesized azatide residue is added dropwise via syringe pump over a period of 30–40 minutes to bispentafluorophenol carbonate (1.1 equivalent; synthesized supra) and 1.1 equivalent dimethylaminopyridine (DMAP; Aldrich) in 0.10 Molar methylene chloride at 25° C. The activated azacarbamate is then further purified by flash chromatography, distillation or crystallization by standard purification methodologies.

Synthesis of Azatide Residue With Val-R-group (FIG. 11; Equation 2):

A solution of 0.098 mole of 2-chloropropane in 0.98 Molar of ethanol was added over a period of 1 hour to a refluxing solution of 0.51 mol of 85% hydrazine hydrate (commercially available from Aldrich company) in 2.55 Molar of ethanol. After a reflux period of,6 hours, the alcohol was removed by distillation. The residue was extracted with ether, the ethereal extracts dried with potassium carbonate and filtered. The crude base, 1.0 equivalents, was next exposed to 1.1 equivalents of di-tert-butyl dicarbonate (commercially available from Aldrich company) in 0.1 Molar methylene chloride and then stirred overnight at 25° C. The solvent was next removed by distillation and the remaining residue was extracted with ether, washed in water (1×) and dried over potassium carbonate and filtered. Product can then be purified by flash chromatography using a methylene chloride: ether/petroleum ether gradient.

Formation of the activated azacarbamate: 1.0 equivalent of the above synthesized azatide residue is added dropwise via syringe pump over a period of 30–40 minutes to bispentafluorophenol carbonate (1.1 equivalent; synthesized supra) and 1.1 equivalent dimethylaminopyridine (DMAP; Aldrich) in 0.10 Molar methylene chloride at 25° C. The activated azacarbamate is then further purified by flash chromatography, distillation or crystallization by standard purification methodologies.

Synthesis of Azatide Residue With Leu-R-group (FIG. 11; Equation 3):

A solution of 0.098 mole of 1-chloro-2-methylpropane (from Aldrich company) in 0.98 Molar of ethanol was added over a period of 1 hour to a refluxing solution of 0.51 mol of 85% hydrazine hydrate (commercially available from Aldrich company) in 2.55 Molar of ethanol. After a reflux period of 6 hours, the alcohol was removed by distillation. The residue was extracted with ether, the ethereal extracts dried with potassium carbonate and filtered. The crude base, 1.0 equivalent, was next exposed to 1.1 equivalents of di-tert-butyl dicarbonate (commercially available from Aldrich company) in 0.1 Molar methylene chloride and then stirred overnight at 25° C. The solvent was next removed by distillation and the remaining residue was extracted with ether, washed in water (1×) and dried over potassium carbonate and filtered. Product can then be purified by flash chromatography using a methylene chloride:ether/ petroleum ether gradient.

Formation of the activated azacarbamate: 1.0 equivalent of the above synthesized azatide residue is added dropwise via syringe pump over a period of 30–40 minutes to bispentafluorophenol carbonate (1.1 equivalent; synthesized supra)

and 1.1 equivalent dimethylaminopyridine (DMAP; Aldrich) in 0.10 Molar methylene chloride at 25° C. The activated azacarbamate is then further purified by flash chromatography, distillation or crystallization by standard purification methodologies.

Synthesis of Azatide Residue With Ile-R-group (FIG. 11; Equation 4):

A solution of 0.098 mole of 2-chlorobutane (from Aldrich company) in 0.98 Molar of ethanol was added over a period of 1 hour to a refluxing solution of 0.51 mol of 85% hydrazine hydrate (commercially available from Aldrich company) in 2.55 Molar of ethanol. After a reflux period of 6 hours, the alcohol was removed by distillation. The residue was extracted with ether, the ethereal extracts dried with potassium carbonate and filtered. The crude base, 1.0 equivalents, was next exposed to 1.1 equivalents of di-tert-butyl dicarbonate (commercially available from Aldrich company) in 0.1 Molar methylene chloride and then stirred overnight at 25° C. The solvent was next removed by distillation and the remaining residue was extracted with ether, washed in water (1×) and dried over potassium carbonate and filtered. Product can then be purified by flash chromatography using a methylene chloride:ether/ petroleum ether gradient.

Formation of the activated azacarbamate: 1.0 equivalent of the above synthesized azatide residue is added dropwise via syringe pump over a period of 30–40 minutes to bispentafluorophenol carbonate (1.1 equivalent; synthesized supra) and 1.1 equivalent dimethylaminopyridine (DMAP; Aldrich) in 0.10 Molar methylene chloride at 25° C. The activated azacarbamate is then further purified by flash chromatography, distillation or crystallization by standard purification methodologies.

Synthesis of Azatide Residue With Pro-R-group (FIG. 11; Equation 5):

A solution of 0.098 mole of pyrazolidine (from Aldrich company) in 0.98 Molar of ethanol was added over a period of 1 hour to a refluxing solution of 0.51 mol of 85% hydrazine hydrate (commercially available from Aldrich company) in 2.55 Molar of ethanol. After a reflux period of 6 hours, the alcohol was removed by distillation. The residue was extracted with ether, the ethereal extracts dried with potassium carbonate and filtered. The crude base, 1.0 equivalent, was next exposed to 1.1 equivalents of di-tert-butyl dicarbonate (commercially available from Aldrich company) in 0.1 Molar methylene chloride and then stirred overnight at 25° C. The solvent was next removed by distillation and the remaining residue was extracted with ether, washed in water (1×) and dried over potassium carbonate and filtered. Product can then be purified by flash chromatography using a methylene chloride: ether/ petroleum ether gradient.

Formation of the activated azacarbamate: 1.0 equivalent of the above synthesized azatide residue is added dropwise via syringe pump over a period of 30–40 minutes to bispentafluorophenol carbonate (1.1 equivalent; synthesized supra) and 1.1 equivalent dimethylaminopyridine (DMAP; Aldrich) in 0.10 Molar methylene chloride at 25° C. The activated azacarbamate is then further purified by flash chromatography, distillation or crystallization by standard purification methodologies.

Synthesis of Azatide Residue With Phe-R-group (FIG. 12; Equation 6):

A solution of 0.098 mole of benzyl chloride in 0.98 Molar of ethanol was added over a period of 1 hour to a refluxing solution of 0.51 mol of 85% hydrazine hydrate (commercially available from Aldrich company) in 2.55 Molar of ethanol. After a reflux period of 6 hours, the alcohol was removed by distillation. The residue was extracted with ether, the ethereal extracts dried with potassium carbonate and filtered. The crude base, 1.0 equivalent, was next exposed to 1.1 equivalents of di-tert-butyl dicarbonate (commercially available from Aldrich company) in 0.1 Molar methylene chloride and then stirred overnight at 25° C. The solvent was next removed by distillation and the remaining residue was extracted with ether, washed in water (1×) and dried over potassium carbonate and filtered. Product can then be purified by flash chromatography using a methylene chloride: ether/petroleum ether gradient.

Formation of the activated azacarbamate: 1.0 equivalent of the above synthesized azatide residue is added dropwise via syringe pump over a period of 30–40 minutes to bispentafluorophenol carbonate (1.1 equivalent; synthesized supra) and 1.1 equivalent dimethylaminopyridine (DMAP; Aldrich) in 0.10 Molar methylene chloride at 25° C. The activated azacarbamate is then further purified by flash chromatography, distillation or crystallization by standard purification methodologies.

Synthesis of Azatide Residue With Trp-R-group (FIG. 12; Equation 7):

A solution of 0.098 mole of chloro-3-methyl-indole (Aldrich company) in 0.98 Molar of ethanol was added over a period of 1 hour to a refluxing solution of 0.51 mol of 85% hydrazine hydrate (commercially available from Aldrich company) in 2.55 Molar of ethanol. After a reflux period of 6 hours, the alcohol was removed by distillation. The residue was extracted with ether, the ethereal extracts dried with potassium carbonate and filtered. The crude base, 1.0 equivalent, was next exposed to 1.1 equivalents of di-tert-butyl dicarbonate (commercially available from Aldrich company) in 0.1 Molar methylene chloride and then stirred overnight at 25° C. The solvent was next removed by distillation and the remaining residue was extracted with ether, washed in water (1×) and dried over potassium carbonate and filtered. Product can then be purified by flash chromatography using a methylene chloride: ether/ petroleum ether gradient.

Formation of the activated azacarbamate: 1.0 equivalent of the above synthesized azatide residue is added dropwise via syringe pump over a period of 30–40 minutes to bispentafluorophenol carbonate (1.1 equivalent; synthesized supra) and 1.1 equivalent dimethylaminopyridine (DMAP; Aldrich) in 0.10 Molar methylene chloride at 25° C. The activated azacarbamate is then further purified by flash chromatography, distillation or crystallization by standard purification methodologies.

Synthesis of Azatide Residue With Met-R-group (FIG. 12; Equation 8):

A solution of 0.098 mole of 1-chloro-2-thiomethyl-ethane (Aldrich company) in 0.98 Molar of ethanol was added over a period of 1 hour to a refluxing solution of 0.51 mol of 85% hydrazine hydrate (commercially available from Aldrich company) in 2.55 Molar of ethanol. After a reflux period of 6 hours, the alcohol was removed by distillation. The residue was extracted with ether, the ethereal extracts dried with potassium carbonate and filtered. The crude base, 1.0 equivalent, was next exposed to 1.1 equivalents of di-tert-butyl dicarbonate (commercially available from Aldrich company) in 0.1 Molar methylene chloride and then stirred overnight at 25° C. The solvent was next removed by distillation and the remaining residue was extracted with ether, washed in water (1×) and dried over potassium carbonate and filtered. Product can then be purified by flash chromatography using a methylene chloride:ether/ petroleum ether gradient.

Formation of the activated azacarbamate: 1.0 equivalent of the above synthesized azatide residue is added dropwise via syringe pump over a period of 30–40 minutes to bispentafluorophenol carbonate (1.1 equivalent; synthesized supra) and 1.1 equivalent dimethylaminopyridine (DMAP; Aldrich) in 0.10 Molar methylene chloride at 25° C. The activated azacarbamate is then further purified by flash chromatography, distillation or crystallization by standard purification methodologies.

Synthesis of Azatide Residue With Gly-R-group (FIG. 12; Equation 9):

A solution of 85% hydrazine hydrate (10 equivalents; commercially available from Aldrich company) in 2.55 Molar of ethanol was exposed to 1.0 equivalent of di-tert-butyl dicarbonate (commercially available from Aldrich company) and then stirred overnight at 25° C. The solvent was next removed by distillation and the remaining residue was extracted with ether, washed in water (1×) and dried over potassium carbonate and filtered. Product can then be purified by flash chromatography using a methylene chloride:ether/petroleum ether gradient.

Formation of the activated azacarbamate: 1.0 equivalent of the above synthesized azatide residue is added dropwise via syringe pump over a period of 30–40 minutes to bispentafluorophenol carbonate (1.1 equivalent; synthesized supra) and 1.1 equivalent dimethylaminopyridine (DMAP; Aldrich) in 0.10 Molar methylene chloride at 25° C. The activated azacarbamate is then further purified by flash chromatography, distillation or crystallization by standard purification methodologies.

Synthesis of Azatide Residue With Ber-R-group (FIG. 12; Equation 10):

Formation of BnO—$CH_2Cl$, used infra, is accomplished by the dropwise addition of 1.1 equivalents of preformed $NaOCH_2Ph$ (formed by the addition of 1.1 equivalents NaH to 1.0 equivalent benzylalcohol in methylene chloride (1.0 M) at 0° C.; 1 hour) to bromochloromethane (Aldrich) in methylene chloride (1.0 M) at 0° C. for 1 hour. The reaction mixture is then quenched with ammonium chloride, washed with water and further purified by flash chromatography to afford Bno—$CH_2Cl$.

A solution of 0.098 mole of Bno—$CH_2Cl$ (synthesized supra) in 0.98 Molar of ethanol was added over a period of 1 hour to a refluxing solution of 0.51 mol of 85% hydrazine hydrate (commercially available from Aldrich company) in 2.55 Molar of ethanol. After a reflux period of 6 hours, the alcohol was removed by distillation. The residue was extracted with ether, the ethereal extracts dried with potassium carbonate and filtered. The crude base, 1.0 equivalent, was next exposed to 1.1 equivalents of di-tert-butyl dicarbonate (commercially available from Aldrich company) in 0.1 Molar methylene chloride and then stirred overnight at 25° C. The solvent was next removed by distillation and the remaining residue was extracted with ether, washed in water (1×) and dried over potassium carbonate and filtered. Product can then be purified by flash chromatography using a methylene chloride: ether/petroleum ether gradient.

Formation of the activated azacarbamate: 1.0 equivalent of the above synthesized azatide residue is added dropwise via syringe pump over a period of 30–40 minutes to bispentafluorophenol carbonate (1.1 equivalent; synthesized supra) and 1.1 equivalent dimethylaminopyridine (DMAP; Aldrich) in 0.10 Molar methylene chloride at 25° C. The activated azacarbamate is then further purified by flash chromatography, distillation or crystallization by standard purification methodologies.

Synthesis of Azatide Residue With Thr-R-group (FIG. 13; Equation 11):

Formation of Bno—CHCl—$CH_3$, used infra, is accomplished by the dropwise addition of 1.1 equivalents of preformed $NaOCH_2Ph$ (formed by the addition of 1.1 equivalents NaH to 1.0 equivalent benzylalcohol in methylene chloride (1.0 M) at 0° C.; 1 hour) to 1,1-dichloroethane (Aldrich) in methylene chloride (1.0 M) at 0° C. for 1 hour. The reaction mixture is then quenched with ammonium chloride, washed with water and further purified by flash chromatography to afford Bno—CHCl—$CH_3$.

A solution of 0.098 mole of Bno—CHCl—$CH_3$ (synthesized supra) in 0.98 Molar of ethanol was added over a period of 1 hour to a refluxing solution of 0.51 mol of 85% hydrazine hydrate (commercially available from Aldrich company) in 2.55 Molar of ethanol. After a reflux period of 6 hours, the alcohol was removed by distillation. The residue was extracted with ether, the ethereal extracts dried with potassium carbonate and filtered. The crude base, 1.0 equivalents, was next exposed to 1.1 equivalents of di-tert-butyl dicarbonate (commercially available from Aldrich company) in 0.1 Molar methylene chloride and then stirred overnight at 25° C. The solvent was next removed by distillation and the remaining residue was extracted with ether, washed in water (1×) and dried over potassium carbonate and filtered. Product can then be purified by flash chromatography using a methylene chloride:ether/petroleum ether gradient.

Formation of the activated azacarbamate: 1.0 equivalent of the above synthesized azatide residue is added dropwise via syringe pump over a period of 30–40 minutes to bispentafluorophenol carbonate (1.1 equivalent; synthesized supra) and 1.1 equivalent dimethylaminopyridine (DMAP; Aldrich) in 0.10 Molar methylene chloride at 25° C. The activated azacarbamate is then further purified by flash chromatography, distillation or crystallization by standard purification methodologies.

Synthesis of Azatide Residue With Cys-R-group (FIG. 13; Equation 12):

Formation of $HSCH_2Cl$ is accomplished by the dropwise addition of 1.1 equivalents of preformed NaSH (Aldrich) to bromochloromethane (Aldrich) in methylene chloride (1.0 M) at 0° C. for 1 hour. Next, a solution of 0.098 mole of $HSCH_2Cl$ (in situ, synthesized supra) in 0.98 Molar of ethanol is added over a period of 1 hour to a refluxing solution of 0.51 mol of 85% hydrazine hydrate (commercially available from Aldrich company) in 2.55 Molar of ethanol. After a reflux period of 6 hours, the alcohol is removed by distillation. The residue is extracted with ether, the ethereal extracts dried with potassium carbonate and filtered. The crude base, 1.0 equivalents, is next exposed to 1.1 equivalents of di-tert-butyl dicarbonate (commercially available from Aldrich company) in 0.1 Molar methylene chloride and then stirred overnight at 25° C. The solvent is next removed by distillation and the remaining residue is extracted with ether, ished in water (1×) and dried over potassium carbonate and filtered. Product can then be purified by flash chromatography using a methylene chloride: ether/petroleum ether gradient.

Formation of the activated azacarbamate: 1.0 equivalent of the above synthesized azatide residue is added dropwise via syringe pump over a period of 30–40 minutes to bispentafluorophenol carbonate (1.1 equivalent; synthesized supra) and 1.1 equivalent dimethylaminopyridine (DMAP; Aldrich) in 0.10 Molar methylene chloride at 0° C. The activated azacarbamate is then further purified by flash chromatography, distillation or crystallization by standard purification methodologies.

To protect the sulfydryl group, an S-sulfenylthiocarbonate derivative is made according to the procedure of Nokihara et al. *J Org. Chem.*, 43, 4893 (1978) which forms the protected azatide residue after standard purification methodologies.

Synthesis of Azatide Residue With Tyr-R-group (FIG. 13; Equation 13):

To a solution of 1.0 equivalent of p-hydroxybenzylbromide in methylene chloride is added 1.1 equivalents of 60% sodium hydride at 0° C. and allowed to stir for 1 hour. Next, 1.1 equivalents of benzyl bromide is added and the mixture is allowed to stir overnight. The mixture is then quenched with water, diluted with ether and purified by distillation. 1.0 equivalents of the compound is next added over a period of 1 hour to a refluxing solution of 0.51 mol of 85% hydrazine hydrate (commercially available from Aldrich company) in 2.55 Molar of ethanol. After a reflux period of 6 hours, the alcohol is removed by distillation. The residue is extracted with ether, the ethereal extracts dried with potassium carbonate and filtered. The crude base, 1.0 equivalents, is next exposed to 1.1 equivalents of di-tert-butyl dicarbonate (commercially available from Aldrich company) in 0.1 Molar methylene chloride and then stirred overnight at 25° C. The solvent is next removed by distillation and the remaining residue is extracted with ether, washed in water (1×) and dried over potassium carbonate and filtered. Product can then be purified by flash chromatography using a methylene chloride:ether/petroleum ether gradient.

Formation of the activated azacarbamate: 1.0 equivalent of the above synthesized azatide residue is added dropwise via syringe pump over a period of 30–40 minutes to bispentafluorophenol carbonate (1.1 equivalent; synthesized supra) and 1.1 equivalent dimethylaminopyridine (DMAP; Aldrich) in 0.10 Molar methylene chloride at 25° C. The activated azacarbamate is then further purified by flash chromatography, distillation or crystallization by standard purification methodologies.

Synthesis of Azatide Residue With Asn-R-group (FIG. 13; Equation 14):

Formation of 2-chloroacetyl-N-9-fluorenylmethylcarbamate, used infra, is formed from protection of 1.0 equivalent 2-chloro-acetamide (Aldrich) with 1.1 equivalents 9-fluorenyl-$CH_2OCOCl$ (Aldrich) in 0.10 M methylene chloride at 0° C. for 1 hour. Product can then be purified by flash chromatography using a methylene chloride:ether/petroleum ether gradient.

Next, a solution of 0.098 mole of 2-chloroacetyl-N-9-fluorenylmethylcarbamate (vida supra) in 0.98 Molar of ethanol was added over a period of 1 hour to a refluxing solution of 0.51 mol of 85% hydrazine hydrate (commercially available from Aldrich company) in 2.55 Molar of ethanol. After a reflux period of 6 hours, the ethanol was removed by distillation. The residue was extracted with ether, the ethereal extracts dried with potassium carbonate and filtered. The crude base, 1.0 equivalent, was next exposed to 1.1 equivalents of di-tert-butyl dicarbonate (commercially available from Aldrich company) in 0.1 Molar methylene chloride and then stirred overnight at 25° C. The solvent was next removed by distillation and the remaining residue was extracted with ether, washed in water (1×) and dried over potassium carbonate and filtered. Product can then be purified by flash chromatography using a methylene chloride:ether/petroleum ether gradient.

Formation of the activated azacarbamate: 1.0 equivalent of the above synthesized azatide residue is added dropwise via syringe pump over a period of 30–40 minutes to bispentafluorophenol carbonate (1.1 equivalent; synthesized supra) and 1.1 equivalent dimethylaminopyridine (DMAP; Aldrich) in 0.10 Molar methylene chloride at 25° C. The activated azacarbamate is then further purified by flash chromatography, distillation or crystallization by standard purification methodologies.

Synthesis of Azatide Residue With Gln-R-group (FIG. 13; Equation 15):

Formation of 3-chloroethyl-N-9-fluorenylmethylcarbamate, used infra, is formed from protection of 1.0 equivalent 3-chloro-ethylamide (Aldrich) with 1.1 equivalents 9-fluorenyl-$CH_2OCOCl$ (Aldrich) in 0.10 M methylene chloride at 0° C. for 1 hour. Product can then be purified by flash chromatography using a methylene chloride:ether/petroleum ether gradient.

Next, a solution of 0.098 mole of 3-chloroethyl-N-9-fluorenylmethylcarbamate (vida supra) in 0.98 Molar of ethanol was added over a period of 1 hour to a refluxing solution of 0.51 mol of 85% hydrazine hydrate (commercially available from Aldrich company) in 2.55 Molar of ethanol. After a reflux period of 6 hours, the ethanol was removed by distillation. The residue was extracted with ether, the ethereal extracts dried with potassium carbonate and filtered. The crude base, 1.0 equivalent, was next exposed to 1.1 equivalents of di-tert-butyl dicarbonate (commercially available from Aldrich company) in 0.1 Molar methylene chloride and then stirred overnight at 25° C. The solvent was next removed by distillation and the remaining residue was extracted with ether, washed in water (1×) and dried over potassium carbonate and filtered. Product can then be purified by flash chromatography using a methylene chloride:ether/petroleum ether gradient.

Formation of the activated azacarbamate: 1.0 equivalent of the above synthesized azatide residue is added dropwise via syringe pump over a period of 30–40 minutes to bispentafluorophenol carbonate (1.1 equivalent; synthesized supra) and 1.1 equivalent dimethylaminopyridine (DMAP; Aldrich) in 0.10 Molar methylene chloride at 25° C. The activated azacarbamate is then further purified by flash chromatography, distillation or crystallization by standard purification methodologies.

Synthesis of Azatide Residue With Asp-R-group (FIG. 14; Equation 16):

Formation of $Bn—O_2CCH_2—OTf$, used infra, is formed from protection of 1.0 equivalent benzylglycolate (Aldrich) with 1.1 equivalents trifluoraceticanhydride (Aldrich) and 1.1 equivalents triethylamine in 0.10 M methylene chloride at 0° C. for 1 hour. Product can then be purified by flash chromatography using a methylene chloride:ether/petroleum ether gradient.

Next, a solution of 0.098 mole of $Bn—O_2CCH_2—OTf$ (vida supra) in 0.98 Molar of ethanol was added over a period of 1 hour to a refluxing solution of 0.51 mol of 85% hydrazine hydrate (commercially available from Aldrich company) in 2.55 Molar of ethanol. After a reflux period of 6 hours, the ethanol was removed by distillation. The residue was extracted with ether, the ethereal extracts dried with potassium carbonate and filtered. The crude base, 1.0 equivalents, was next exposed to 1.1 equivalents of di-tert-butyl dicarbonate (commercially available from Aldrich company) in 0.1 Molar methylene chloride and then stirred overnight at 25° C. The solvent was next removed by distillation and the remaining residue was extracted with ether, washed in water (1×) and dried over potassium carbonate and filtered. Product can then be purified by flash chromatography using a methylene chloride:ether/petroleum ether gradient.

Formation of the activated azacarbamate: 1.0 equivalent of the above synthesized azatide residue is added dropwise via syringe pump over a period of 30–40 minutes to bispentafluorophenol carbonate (1.1 equivalent; synthesized supra) and 1.1 equivalent dimethylaminopyridine (DMAP; Aldrich) in 0.10 Molar methylene chloride at 250° C. The activated azacarbamate is then further purified by flash chromatography, distillation or crystallization by standard purification methodologies.

Synthesis of Azatide Residue With Glu-R-group (FIG. 14; Equation 17):

Formation of Bn-O$_2$CCH$_2$CH$_2$-OTf, used infra, is formed from protection of 1.0 equivalent benzyl-3-hydroxypropanoate (Aldrich) with 1.1 equivalents trifluoroacetic anhydride (Aldrich) and 1.1 equivalents triethylamine in 0.10 M methylene chloride at 0° C. for 1 hour. Product can then be purified by flash chromatography using a methylene chloride:ether/petroleum ether gradient.

Next, a solution of 0.098 mole of Bn—O$_2$CCH$_2$CH$_2$-OTf (vida supra) in 0.98 Molar of ethanol was added over a period of 1 hour to a refluxing solution of 0.51 mol of 85% hydrazine hydrate (commercially available from Aldrich company) in 2.55 Molar of ethanol. After a reflux period of 6 hours, the ethanol was removed by distillation. The residue was extracted with ether, the ethereal extracts dried with potassium carbonate and filtered. The crude base, 1.0 equivalents, was next exposed to 1.1 equivalents of di-tert-butyl dicarbonate (commercially available from Aldrich company) in 0.1 Molar methylene chloride and then stirred overnight at 25° C. The solvent was next removed by distillation and the remaining residue was extracted with ether, washed in water (1×) and dried over potassium carbonate and filtered. Product can then be purified by flash chromatography using a methylene chloride:ether/petroleum ether gradient.

Formation of the activated azacarbamate: 1.0 equivalent of the above synthesized azatide residue is added dropwise via syringe pump over a period of 30–40 minutes to bispentafluorophenol carbonate (1.1 equivalent; synthesized supra) and 1.1 equivalent dimethylaminopyridine (DMAP; Aldrich) in 0.10 Molar methylene chloride at 25° C. The activated azacarbamate is then further purified by flash chromatography, distillation or crystallization by standard purification methodologies.

Synthesis of Azatide Residue With Lys-R-group (FIG. 14; Equation 18):

Formation of (9-Fluor)—NH—(CH$_2$)$_3$CH$_2$OTf, used infra, is formed from protection of 1.0 equivalent NH$_2$(CH$_2$)$_3$CH$_2$OH (4-hydroxybutylamine; Aldrich) with 1.1 equivalents 9-fluorenyl-CH$_2$OCOCl (Aldrich) in 0.10 M methylene chloride at 0° C. for 1 hour. Product can then be purified by flash chromatography using a methylene chloride:ether/petroleum ether gradient. Next, 1.0 equivalent of the product is reacted with 1.1 equivalents trifluoroacetic anhydride (Aldrich) and 1.1 equivalents triethylamine in 0.10 M methylene chloride at 0° C. for 1 hour. Product can then be purified by flash chromatography using a methylene chloride:ether/petroleum ether gradient.

Next, a solution of 0.098 mole of (9-Fluor)—NH—(CH$_2$)$_3$CH$_2$OTf (vida supra) in 0.98 Molar of ethanol was added over a period of 1 hour to a refluxing solution of 0.51 mol of 85% hydrazine hydrate (commercially available from Aldrich company) in 2.55 Molar of ethanol. After a reflux period of 6 hours, the ethanol was removed by distillation. The residue was extracted with ether, the ethereal extracts dried with potassium carbonate and filtered. The crude base, 1.0 equivalents, was next exposed to 1.1 equivalents of di-tert-butyl dicarbonate (commercially available from Aldrich company) in 0.1 Molar methylene chloride and then stirred overnight at 25° C. The solvent was next removed by distillation and the remaining residue was extracted with ether, washed in water (1×) and dried over potassium carbonate and filtered. Product can then be purified by flash chromatography using a methylene chloride:ether/ petroleum ether gradient.

Formation of the activated azacarbamate: 1.0 equivalent of the above synthesized azatide residue is added dropwise via syringe pump over a period of 30–40 minutes to bispentafluorophenol carbonate (1.1 equivalent; synthesized supra) and 1.1 equivalent dimethylaminopyridine (DMAP; Aldrich) in 0.10 Molar methylene chloride at 25° C. The activated azacarbamate is then further purified by flash chromatography, distillation or crystallization by standard purification methodologies.

Synthesis of Azatide Residue With Arg-R-group (FIG. 14; Equation 19):

Formation of (9-Fluor) —NH—CNH—NH—(CH$_2$)$_2$CH$_2$OTf, used infra, is formed from protection of 1.0 equivalent NH2-CNH—NH—(CH$_2$) 2CH$_2$OH (Aldrich) with 1.1 equivalents 9-fluorenyl-CH$_2$OCOCl (Aldrich) in 0.10 M methylene chloride at 0° C. for 1 hour. Product can then be purified by flash chromatography using a methylene chloride:ether/petroleum ether gradient. Next, 1.0 equivalent of the product is reacted with 1.1 equivalents trifluoroacetic anhydride (Aldrich) and 1.1 equivalents triethylamine in 0.10 M methylene chloride at 0° C. for 1 hour. Product can then be purified by flash chromatography using a methylene chloride:ether/petroleum ether gradient.

Next, a solution of 0.098 mole of (9-Fluor)—NH—CNH—NH—(CH$_2$)$_2$CH$_2$OTf (vida supra) in 0.98 Molar of ethanol was added over a period of 1 hour to a refluxing solution of 0.51 mol of 85% hydrazine hydrate (commercially available from Aldrich company) in 2.55 Molar of ethanol. After a reflux period of 6 hours, the ethanol was removed by distillation. The residue was extracted with ether, the ethereal extracts dried with potassium carbonate and filtered. The crude base, 1.0 equivalents, was next exposed to 1.1 equivalents of di-tert-butyl dicarbonate (commercially available from Aldrich company) in 0.1 Molar methylene chloride and then stirred overnight at 25° C. The solvent was next removed by distillation and the remaining residue was extracted with ether, washed in water (1×) and dried over potassium carbonate and filtered. Product can then be purified by flash chromatography using a methylene chloride:ether/petroleum ether gradient.

Formation of the activated azacarbamate: 1.0 equivalent of the above synthesized azatide residue is added dropwise via syringe pump over a period of 30–40 minutes to bispentafluorophenol carbonate (1.1 equivalent; synthesized supra) and 1.1 equivalent dimethylaminopyridine (DMAP; Aldrich) in 0.10 Molar methylene chloride at 25° C. The activated azacarbamate is then further purified by flash chromatography, distillation or crystallization by standard purification methodologies.

Synthesis of Azatide Residue With His-R-group (FIG. 14; Equation 20)

Formation of 4-trifluoracetoxymethylimidazole-3-N-(9-fluorenylcarbamate), used infra, is formed from protection of 1.0 equivalent 4-hydroxymethylimidazole (Aldrich) with 1.1 equivalents 9-fluorenyl-CH$_2$OCOCl (Aldrich) in 0.10 M methylene chloride at 0° C. for 1 hour. Product can then be purified by flash chromatography using a methylene chloride: ether/petroleum ether gradient. Next, 1.0 equivalent of the product is reacted with 1.1 equivalents trifluoracetic anhydride (Aldrich) and 1.1 equivalents triethylamine in 0.10 M methylene chloride at 0° C. for 1 hour. Product can then be purified by flash chromatography using a methylene chloride:ether/petroleum ether gradient.

Next, a solution of 0.098 mole of 4-trifluoracetoxymethylimidazole-3-N-(9-fluorenyl-carbamate) (vida supra) in 0.98 Molar of ethanol was added over a period of 1 hour to a refluxing solution of 0.51 mol of 85% hydrazine hydrate (commercially available from Aldrich company) in 2.55 Molar of ethanol. After a reflux period of 6 hours, the ethanol was removed by distillation. The residue was extracted with ether, the ethereal extracts dried with potassium carbonate and filtered. The crude base, 1.0 equivalents, was next exposed to 1.1 equivalents of di-tert-butyl dicarbonate (commercially available from Aldrich company) in 0.1 Molar methylene chloride and then stirred overnight at 25° C. The solvent was next removed by distillation and the remaining residue was extracted with ether, washed in water (1×) and dried over potassium carbonate and filtered. Product can then be purified by flash chromatography using a methylene chloride:ether/petroleum ether gradient.

Formation of the activated azacarbamate: 1.0 equivalent of the above synthesized azatide residue is added dropwise via syringe pump over a period of 30–40 minutes to bispentafluorophenol carbonate (1.1 equivalent; synthesized supra) and 1.1 equivalent dimethylaminopyridine (DMAP; Aldrich) in 0.10 Molar methylene chloride at 25° C. The activated azacarbamate is then further purified by flash chromatography, distillation or crystallization by standard purification methodologies.

What is claimed is:

1. A process for producing precursors of a combinatorial oligoazatide library comprising the following steps:

Step A: providing a soluble homopolymer support with a linker unit attached to said soluble homopolymer support in each of "n" reaction vessels; then Step B: providing "n" Boc-protected aza-amino acids; then Step C: reacting each of the "n" Boc-protected aza-amino acid of said Step B with a carbonyl activation element for producing an activated carbamate of the Boc-protected aza-amino acids capable of coupling with the soluble homopolymer support or with a nascent protected chain thereon, the carbonyl activation element being bis-pentafluorophenyl carbonate; then Step D: adding one of the "n" activated carbamates of said Step C to each of the "n" reaction vessels and coupling the soluble homopolymer support of said Step A with the activated carbamate of said Step C for producing the nascent protected chain in each of the "n" reaction vessels; and then Step E: washing each of the nascent protected chain by precipitation of the soluble homopolymer, thus producing precursors of the combinatorial oligoazatide library.

2. A process for producing a combinatorial oligoazatide library comprising the following steps:

Step A: providing a soluble homopolymer support with a linker unit attached to said soluble homopolymer support in each of "n" reaction vessels; then Step B: providing "n" Boc-protected aza-amino acids; then Step C: reacting each of the "n" Boc-protected aza-amino acid of said Step B with a carbonyl activation element for producing an activated carbamate of the Boc-protected aza-amino acids capable of coupling with the soluble homopolymer support or with a nascent protected chain thereon, the carbonyl activation element being bis-pentafluorophenyl carbonate; then Step D: adding one of the "n" activated carbamates of said Step C to each of the "n" reaction vessels and coupling the soluble homopolymer support of said Step A with the activated carbamate of said Step C for producing the nascent protected chain in each of the "n" reaction vessels; and then Step E: washing each of the nascent protected chain by precipitation of the soluble homopolymer; then Step F: saving and cataloging an aliquot from each of the "n" reaction vessels; then Step G: pooling all "n" of the reaction vessels into a common pot for forming a mixture of nascent protected chains; then Step H: deprotecting the nascent protected chain in each of the "n" reaction vessels using a mild acid for producing nascent deprotected chains; then Step I: washing each of the nascent deprotected chains by precipitation of the soluble homopolymer;

Step J: equally aliquoting the mixture of nascent deprotected chains from the common pot into the "n" reaction vessels; then Step K: extending the nascent deprotected chains of said Step J by repeating steps A through I "m" times wherein $1 \leq m \leq 100$ and wherein the soluble homopolymer support of said Steps A and D is replaced with the nascent deprotected chain of said Step I for producing extended deprotected chains; and then Step L: decoupling and separating the extended deprotected chains in each of the "n" reaction vessels of said Step J from the soluble support by hydrogenation and precipitation, thus producing the combinatorial oligoazatide library.

* * * * *